US010418567B2

(12) United States Patent
Yen et al.

(10) Patent No.: US 10,418,567 B2
(45) Date of Patent: Sep. 17, 2019

(54) ORGANIC COMPOUND FOR ORGANIC EL DEVICE AND USING THE SAME

(71) Applicants: Feng-Wen Yen, Taipei (TW); Tsun-Yuan Huang, Chiayi (TW)

(72) Inventors: Feng-Wen Yen, Taipei (TW); Tsun-Yuan Huang, Chiayi (TW)

( * ) Notice: Subject to any disclaimer, the term of this patent is extended or adjusted under 35 U.S.C. 154(b) by 364 days.

(21) Appl. No.: 15/387,673

(22) Filed: Dec. 22, 2016

(65) Prior Publication Data

US 2018/0182978 A1 Jun. 28, 2018

(51) Int. Cl.

*H01L 51/00* (2006.01)
*C09K 11/06* (2006.01)
*C09K 11/02* (2006.01)
*C07D 495/04* (2006.01)

(52) U.S. Cl.

CPC ........ *H01L 51/0074* (2013.01); *C07D 495/04* (2013.01); *C09K 11/02* (2013.01); *C09K 11/06* (2013.01); *H01L 51/0067* (2013.01); *H01L 51/0071* (2013.01); *C09K 2211/1007* (2013.01); *C09K 2211/1014* (2013.01); *C09K 2211/1044* (2013.01); *C09K 2211/1059* (2013.01); *C09K 2211/1092* (2013.01)

(58) Field of Classification Search

None
See application file for complete search history.

(56) References Cited

U.S. PATENT DOCUMENTS 8,816,100 B2 8/2014 Takimiya et al.
9,018,398 B2 4/2015 Takimiya et al.

FOREIGN PATENT DOCUMENTS

CN 103664995 * 3/2014 .......... C07D 519/00
JP 2013159584 A * 8/2013 .......... C07D 493/04

OTHER PUBLICATIONS

Poulsen et al. "Two-Photon Singlet Oxygen Sensitizers: Quantifying, Modeling, and Optimizing the Two-Photon Absorption Cross Section" J. Phys. Chem. A 2001, 105, 11488-11495. (Year: 2001).*

(Continued)

*Primary Examiner* — Robert S Loewe

(57) ABSTRACT

The present invention discloses an organic material represented by the following formula (1) or formula (2), the organic EL device employing the organic compound as light emitting host of emitting lay and/or an electron transporting layer, and/or a hole blocking layer, and/or a delayed fluorescence material of emitting layer can display good performance.

formula(1)

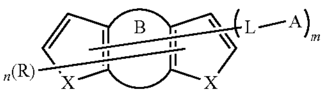

formula(2)

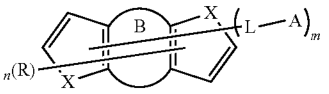

wherein A is an electron acceptor moiety, B represents a fused ring hydrocarbon units with two or three rings; m, n, L, and X are the same definition as described in the present invention.

13 Claims, 1 Drawing Sheet

(56) References Cited

OTHER PUBLICATIONS

Fredericksen et al. "Two-Photon Photosensitized Production of Singlet Oxygen" J. Am. Chem. Soc. 2001, 123, 1215-1221. (Year: 2001).*
Shinamura et al. "Synthesis, Properties, Crystal Structures, and Semiconductor Characteristics of Napththo[1,2-b:5,6-b']dithiophene and diselenophene Derivatives" J. Org. Chem. 2010, 75, 1228-1234. (Year: 2010).*

* cited by examiner

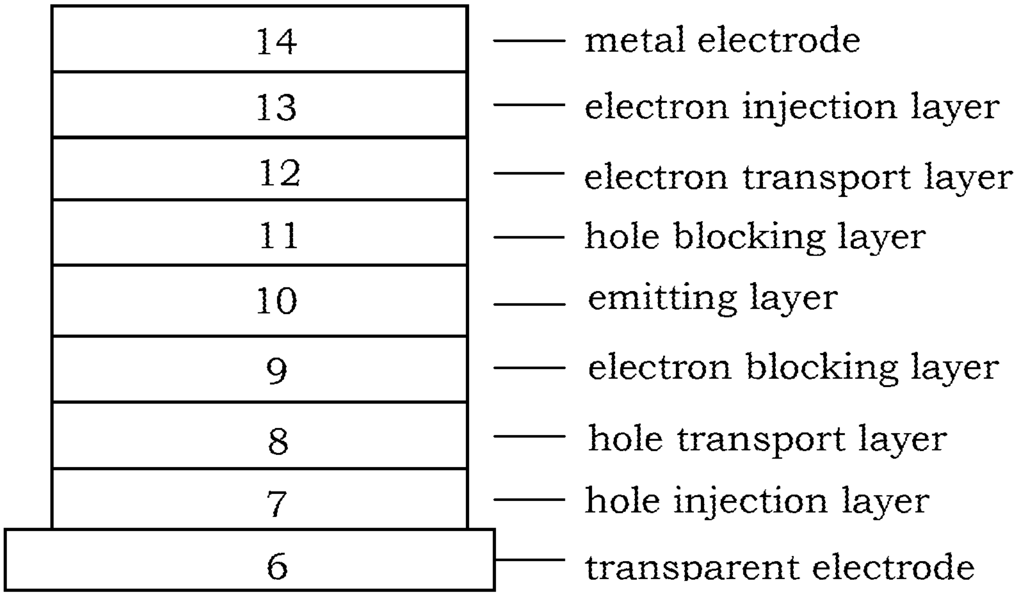
14
metal electrode
13
electron injection layer
12
electron transport layer
11
hole blocking layer
10
emitting layer
9
electron blocking layer
8
hole transport layer
7
hole injection layer
6
transparent electrode

ORGANIC COMPOUND FOR ORGANIC EL DEVICE AND USING THE SAME

FIELD OF INVENTION

Provided generally are luminescent organic material that may be used in organic electroluminescence (herein referred to as organic EL) device. The compound may exhibit delayed fluorescence. The present invention generally relates to a compound and organic EL device using the compound. More specifically, the present invention relates to the compound having general formula (1) or formula (2), an organic EL device employing the material as delayed fluorescence material of emitting layer and/or phosphorescent light emitting host of emitting layer, and/or an electron transporting layer, and/or a hole blocking layer can display excellent performance.

BACKGROUND OF THE INVENTION

The first observation of electroluminescence in organic materials were in the early 1950s by Andre Bernanose and co-workers at the Nancy-University in France. Martin Pope and his co-workers at New York University first observed direct current (DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer (HTL), an emitting layer (EML), an electron transporting layer (ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO (lowest unoccupied molecular orbital) and holes will be injected from an anode into a HOMO (highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden, thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%. The spin-orbit interactions is finished by some heavy atom such as iridium, rhodium, platinum, palladium and the phosphorescent transition may be observed from an excited MLCT (metal to ligand charge transfer) state of organic metallic complexes.

A new type of fluorescent organic EL device incorporating mechanism of thermally activated delayed fluorescence (TADF) has been developed by Adachi and coworkers is a promising way to obtain a high efficiency of exciton formation by converting spin-forbidden triplet excitons up to the singlet level by the mechanism of reverse intersystem crossing (RISC) by using a material having a small energy gap between the singlet level and the triplet level. However, further improvement in luminous efficiency of the organic EL device in a high current density region is still desired.

The organic EL utilizes both triplet and singlet excitons. Cause of longer lifetime and the diffusion length of triplet excitons compared to those of singlet excitons, the phosphorescent organic EL generally need an additional hole blocking layer (HBL) between the emitting layer (EML) and the electron transporting layer (ETL) or electron blocking layer (EBL) between the emitting layer (EML) and the hole transporting layer (HTL). The purpose of the use of HBL or EBL is to confine the recombination of injected holes and electrons and the relaxation of created excitons within the EML, hence the device's efficiency can be improved. To meet such roles, the hole blocking materials or electron blocking materials must have HOMO (highest occupied molecular orbital) and LUMO (lowest unoccupied molecular orbital) energy levels suitable to block hole or electron transport from the EML to the ETL or the HTL.

For full-colored flat panel displays in AMOLED or OLED lighting panel the material used for the phosphorescent host for emitting layer are still unsatisfactory in half-lifetime, efficiency and driving voltage for industrial practice use. Besides, in order to display excellent performance of organic EL devices, the phosphorescent light emitting host material need to collocate with other organic thin film layer such as hole blocking layer and electron transporting layer to get lower power consumption, longer half-life time and higher efficiency. Therefore, there is a demand for designing and developing novel material for organic EL devices.

Recently, attention has been drawn to compound having acenedi chalcogenophene as a basic skeleton such as naphthadithiophene, benzodi thiophene, anthradithiophene, and the like especially as compound for organic semiconductors due to their high electron mobility, the high on/off current ratio, and the excellent storage stability discloses from U.S. Pat. No. 8,816,100B2, U.S. Pat. No. 9,447,111B2. Although such compound are widely used in organic semiconductors but they have not been used in organic EL device, we employ acenedichalcogenophene as a basic donor skeleton and linked to some efficient acceptors such as formula (3) to formula (12) in the present invention to form series of dipolar material as formula (1) or formula (2), those organic materials could be used as delayed fluorescence material of emitting layer and/or phosphorescent light emitting host of emitting layer, and/or an electron transporting layer, and/or a hole blocking layer for organic EL device can display good performance.

SUMMARY OF THE INVENTION

According to the reasons described above, the present invention has the objective of resolving such problems of the prior art and offering a light emitting device which is excellent in its thermal stability, high luminance efficiency and long half-life time. The present invention disclose an organic material having general formula (1) or formula (2), used as delayed fluorescence material of emitting layer and/or phosphorescent light emitting host of emitting layer, and/or an electron transporting layer, and/or a hole blocking layer having good charge carrier mobility and excellent operational durability can lower driving voltage and power consumption, increasing efficiency and half-life time of organic EL device.

The present invention has the economic advantages for industrial practice. Accordingly, the present invention discloses the organic material which can be used for organic EL device is disclosed. The mentioned the organic material is represented by the following formula (1) or formula (2):

formula(1)

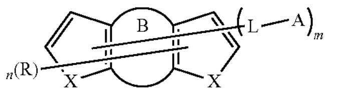

formula(2)

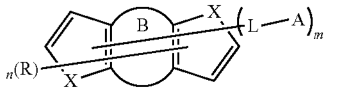

wherein A is an electron acceptor moiety represented from formula (3) to formula (12)

formula(3)

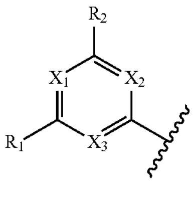

formula(4)

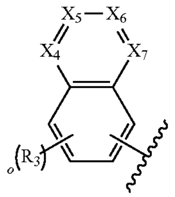

formula(5)

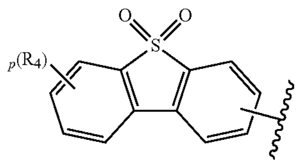

formula(6)

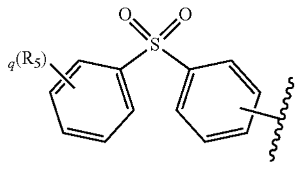

formula(7)

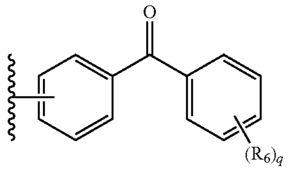

formula(8)

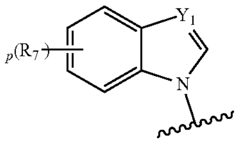

-continued formula(9)

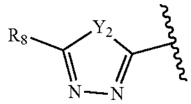

formula(10)

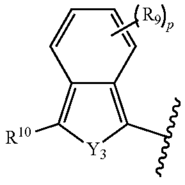

formula(11)

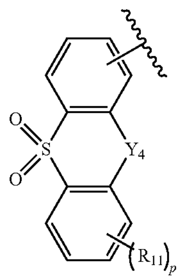

formula(12)

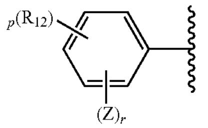

L represents a single bond or a substituted or unsubstituted divalent arylene group having 6 to 30 ring carbon atoms, m represents an integer of 1 to 4, n represents an integer of 1 to 3, X independently represents an oxygen atom, a sulfur atom and a selenium atom, B represents a fused ring hydrocarbon units with two or three rings; o represents an integer of 0 to 3, p represents an integer of 0 to 4, q represents an integer of 0 to 5, r represents an integer of 1 to 5, $Y_1$ to $Y_4$ is a divalent bridge selected from the atom or group consisting from O, S, $C(R_{13})(R_{14})$, $NR_{15}$, and $Si(R_{16})(R_{17})$; $X_1$ to $X_7$ represent a nitrogen atom or $C(R_8)$, and each $R_8$ represents a hydrogen, a phenyl, a substituted or unsubstituted alkyl group having 1 to 30 carbon atoms, and a substituted or unsubstituted aryl group having 6 to 30 carbon atoms; Z represents a cyano group, R and $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

BRIEF DESCRIPTION OF THE DRAWINGS

FIG. 1 show one example of organic EL device in the present invention, wherein 6 is transparent electrode, 14 is metal electrode, 7 is hole injection layer which is deposited onto 6, 8 is hole transport layer which is deposited onto 7, 9 is electron blocking layer which is deposited onto 8, 10 is emitting layer which is deposited onto 9, 11 is hole blocking layer which is deposited onto 10, 12 is electron transport layer which is deposited on to 11, and 13 is electron injection layer which is deposited on to 12.

DESCRIPTION OF THE PREFERRED EMBODIMENTS

What probed into the invention is the organic material for organic EL device using the material. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, the organic material which can be used as delayed fluorescence material of emitting layer and/or phosphorescent light emitting host of emitting layer, and/or an electron transporting layer, and/or a hole blocking layer for organic EL device are disclosed. The mentioned the organic material represented by the following formula (1) or formula (2):

formula(1)

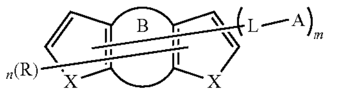

formula(2)

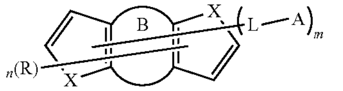

wherein A is an electron acceptor moiety represented from formula (3) to formula (12)

formula(3)

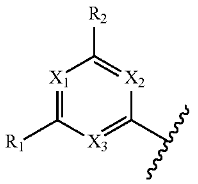

formula(4)

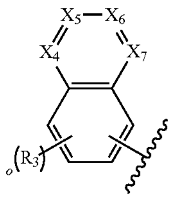

formula(5)

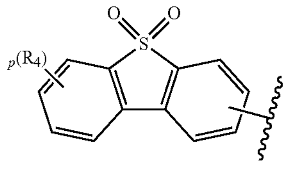

formula(6)

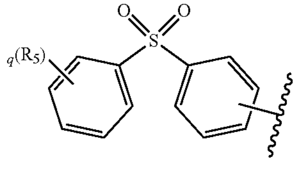

-continued formula(7)

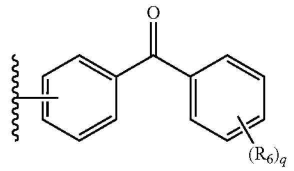

formula(8)

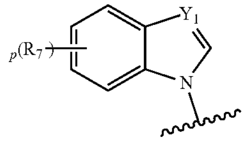

formula(9)

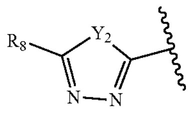

formula(10)

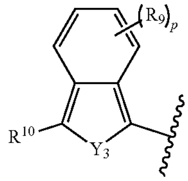

formula(11)

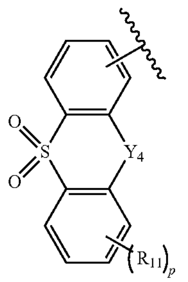

formula(12)

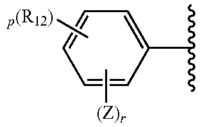

L represents a single bond or a substituted or unsubstituted divalent arylene group having 6 to 30 ring carbon atoms, m represents an integer of 1 to 4, n represents an integer of 1 to 3, X independently represents an oxygen atom, a sulfur atom and a selenium atom, B represents a fused ring hydrocarbon units with two or three rings; o represents an integer of 0 to 3, p represents an integer of 0 to 4, q represents an integer of 0 to 5, r represents an integer of 1 to 5, $Y_1$ to $Y_4$ is a divalent bridge selected from the atom or group consisting from O, S, $C(R_{13})(R_{14})$, $NR_{15}$, and $Si(R_{16})(R_{17})$; $X_1$ to $X_7$ represent a nitrogen atom or $C(R_8)$, and each R-represents a hydrogen, a phenyl, a substituted or unsubstituted alkyl group having 1 to 30 carbon atoms, and a substituted or unsubstituted aryl group having 6 to 30 carbon atoms; Z represents a cyano group, R and $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

According to the above-mentioned the organic material formula (1) or formula (2), wherein the organic material formula (2) is represented by the following formula (13) to formula (15):

formula(13)

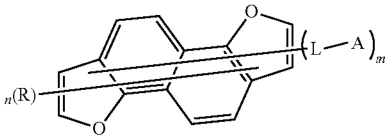

formula(14)

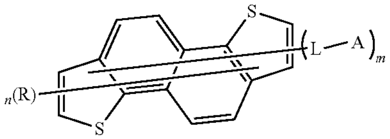

formula(15)

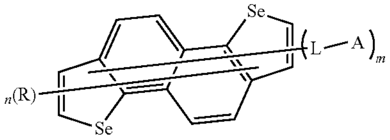

wherein A is an electron acceptor moiety represented from formula (3) to formula (12)

formula(3)

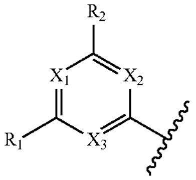

formula(4)

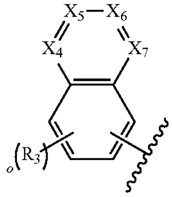

formula(5)

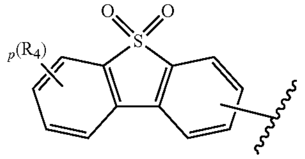

formula(6)

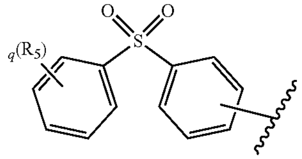

formula(7)

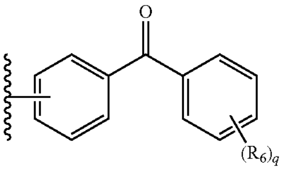

-continued formula(8)

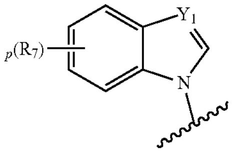

formula(9)

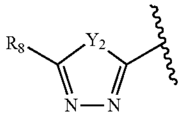

formula(10)

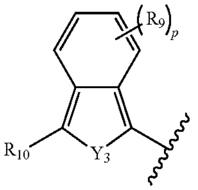

formula(11)

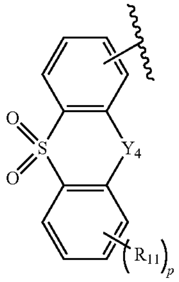

formula(12)

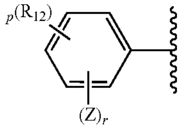

L represents a single bond or a substituted or unsubstituted divalent arylene group having 6 to 30 ring carbon atoms, m represents an integer of 1 or 2, n represents an integer of 1 to 3, o represents an integer of 0 to 3, p represents an integer of 0 to 4, q represents an integer of 0 to 5, r represents an integer of 1 to 5, $Y_1$ to $Y_4$ is a divalent bridge selected from the atom or group consisting from O, S, $C(R_{13})(R_{14})$, $NR_{15}$, and $Si(R_{16})(R_{17})$; $X_1$ to $X_7$ represent a nitrogen atom or $C(R_8)$, and each $R_8$ represents a hydrogen, a phenyl, a substituted or unsubstituted alkyl group having 1 to 30 carbon atoms, and a substituted or unsubstituted aryl group having 6 to 30 carbon atoms; Z represents a cyano group, R and $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

In this embodiment, some organic materials are shown below:

C1
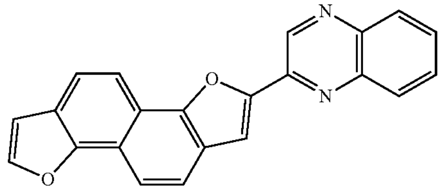
C2
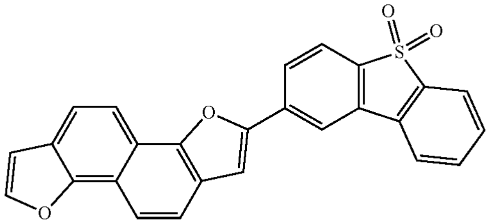
C3
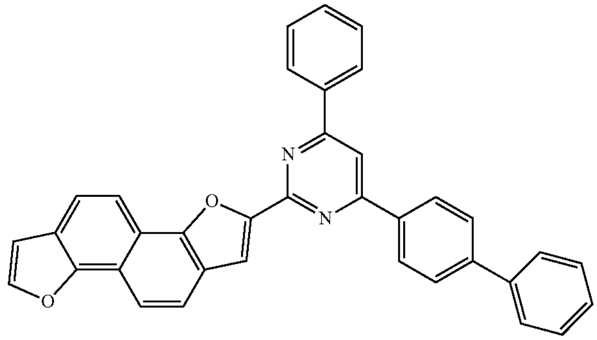
C4
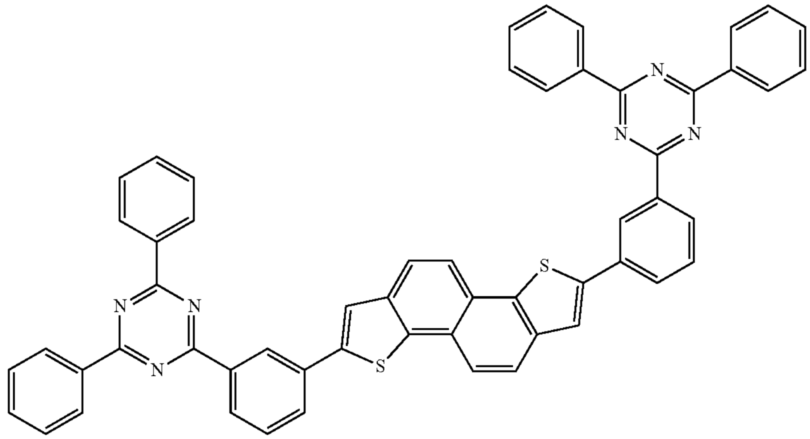
C5
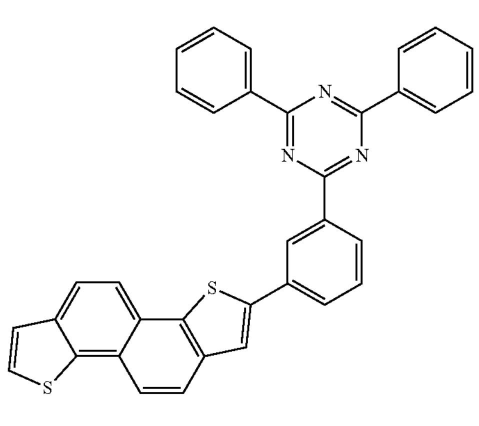
C6
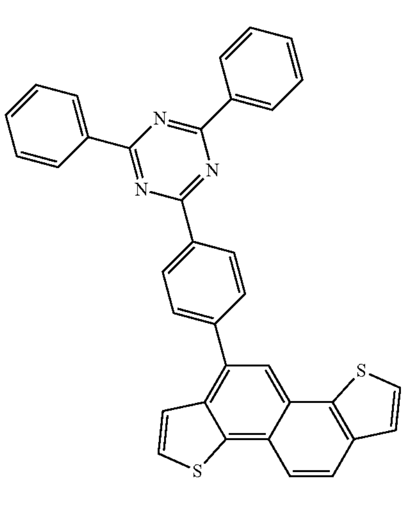

-continued
C7
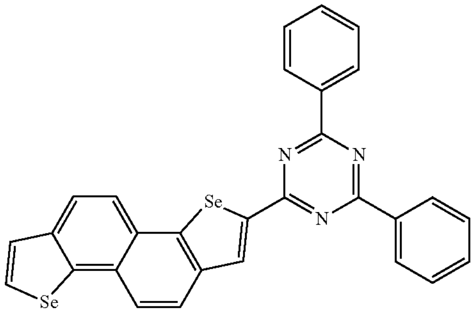
C8
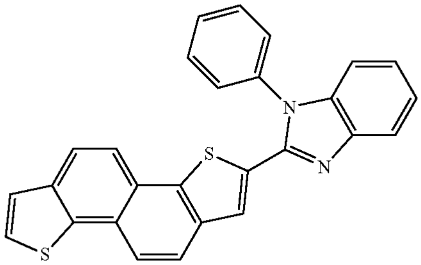
C9
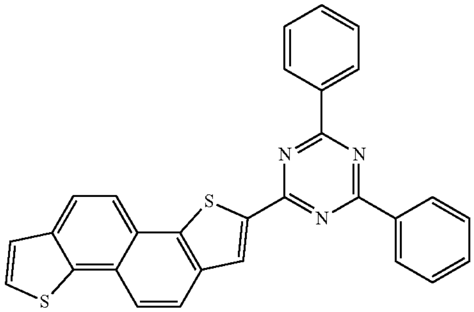
C10
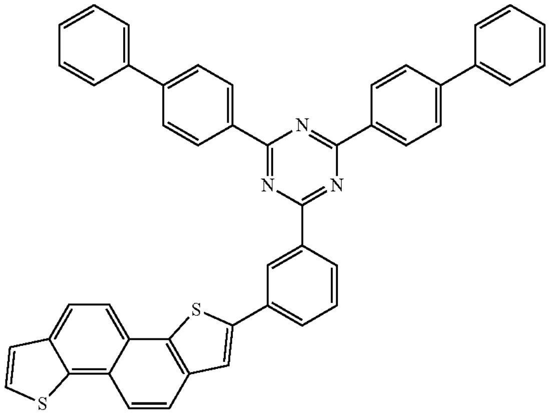
C11
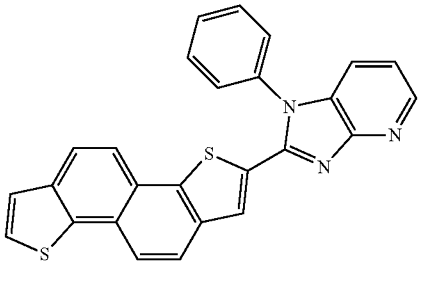
C12
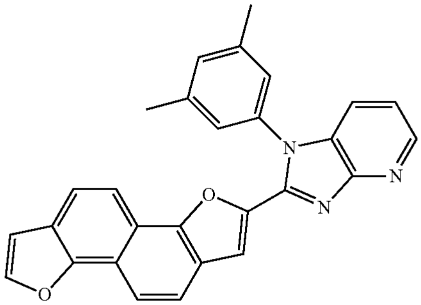
C13
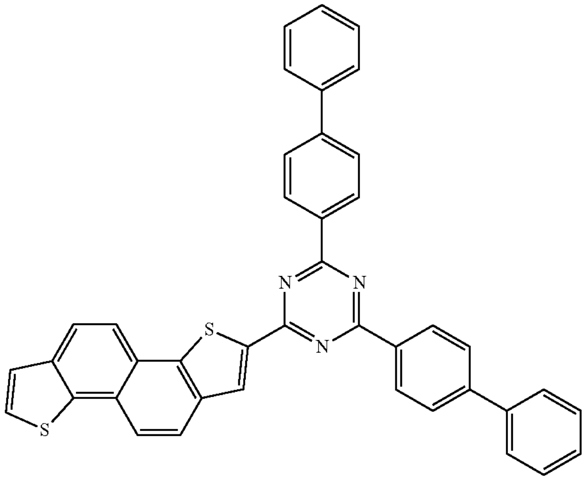

-continued
C14
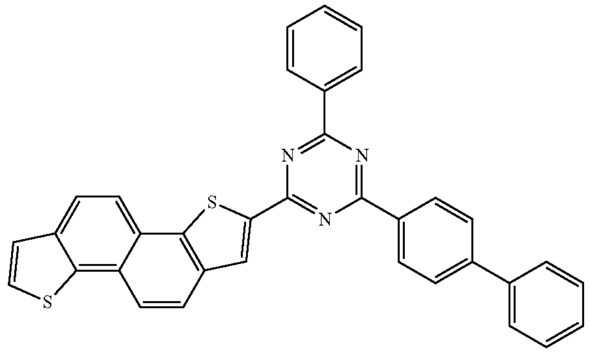
C15
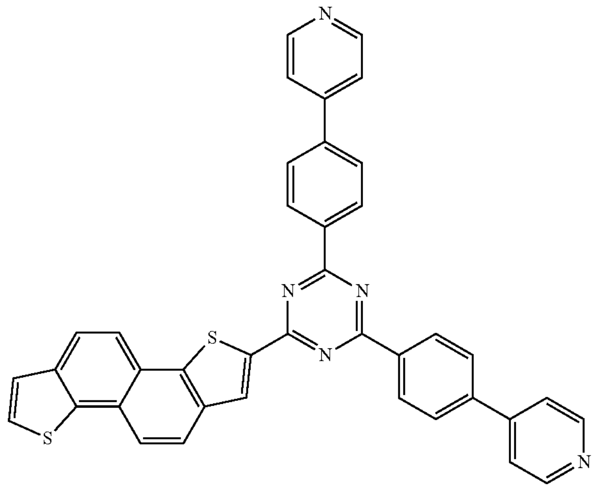
C16
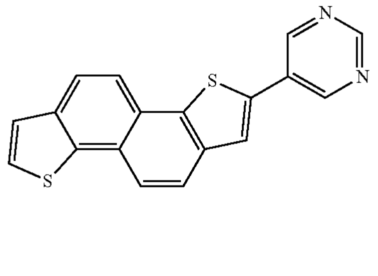
C17
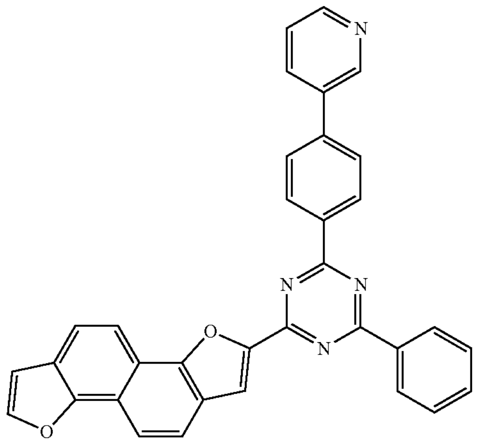

-continued
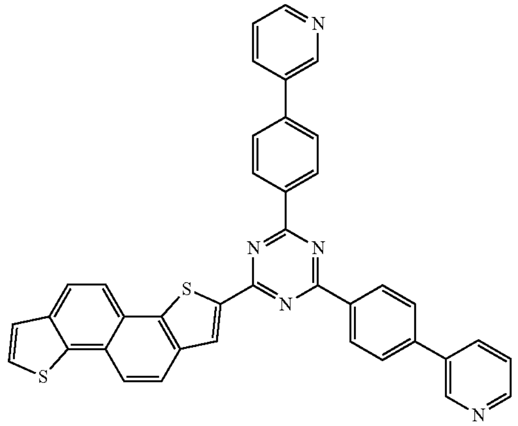
C18
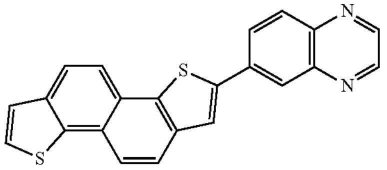
C19
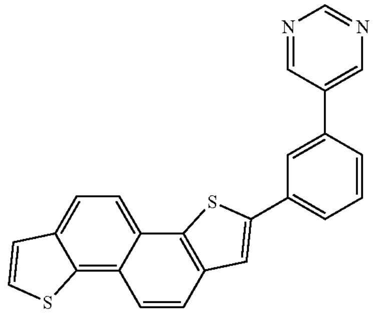
C20
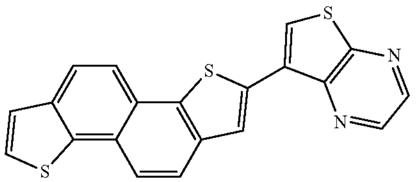
C21
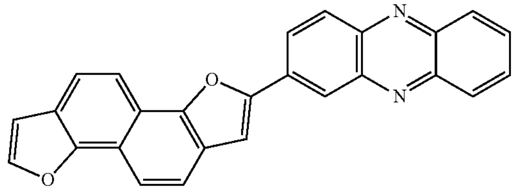
C22
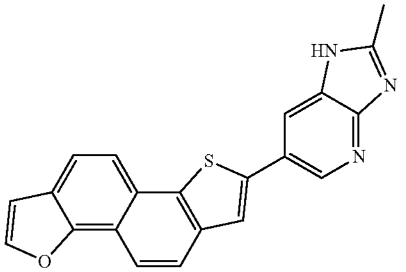
C23
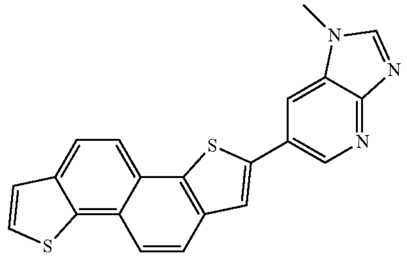
C24
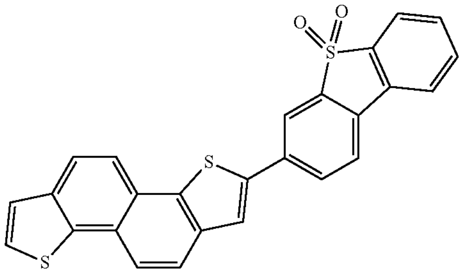
C25
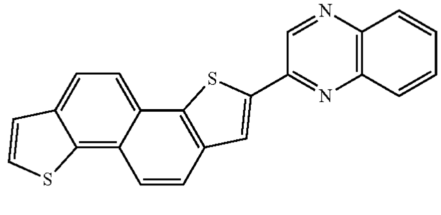
C26
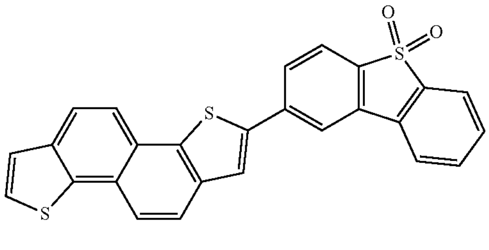
C27

-continued
C28
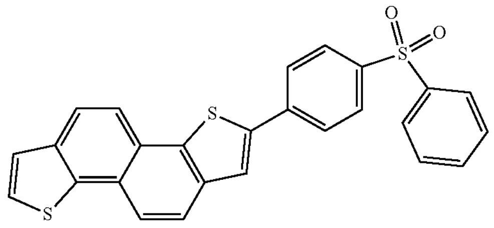
C29
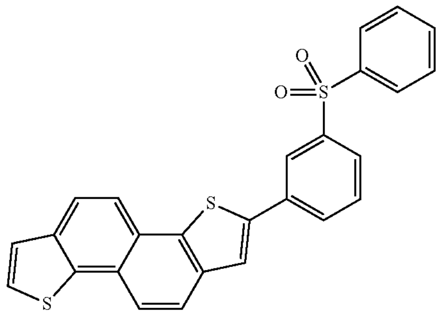
C30
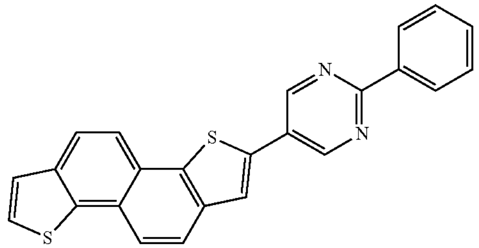
C31
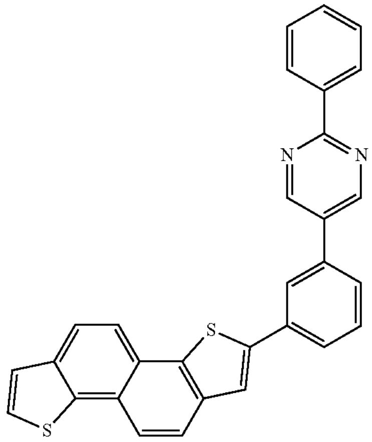
C32
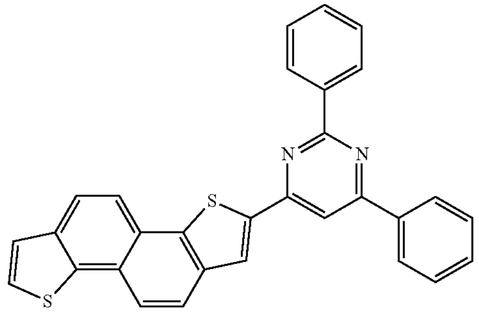
C33
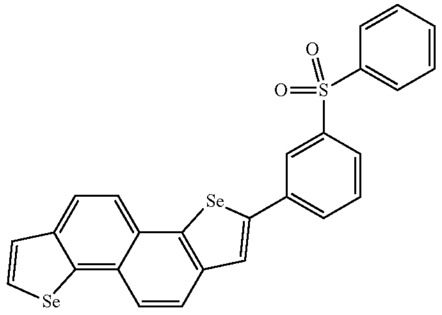
C34
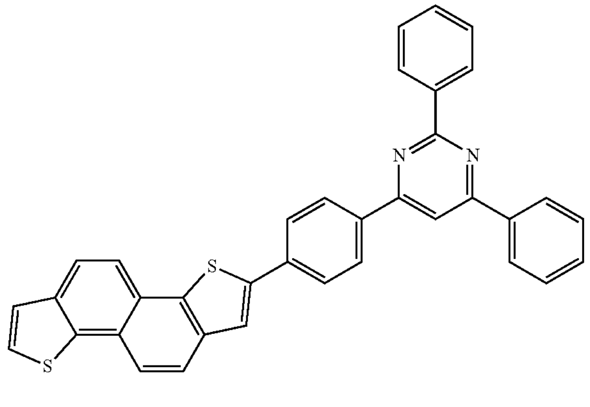

-continued
C35
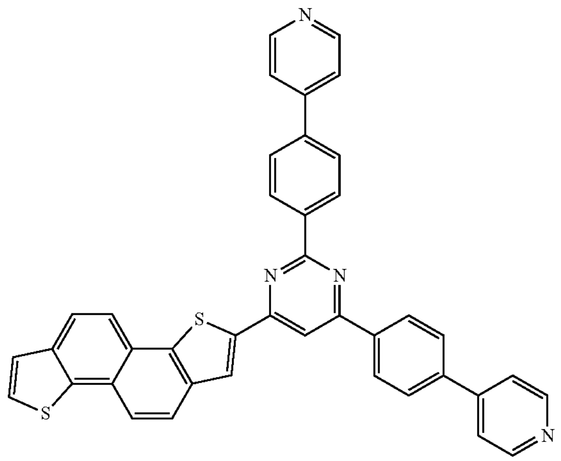
C36
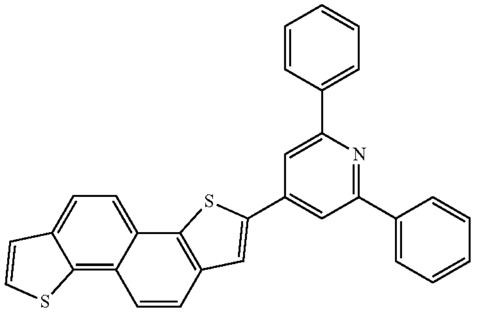
C37
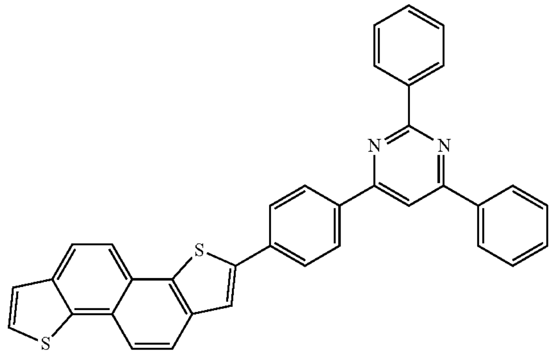
C38
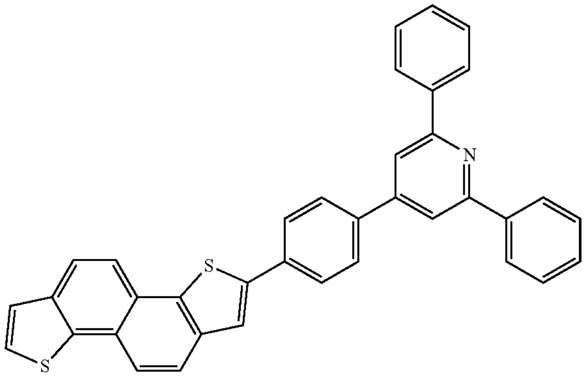
C39
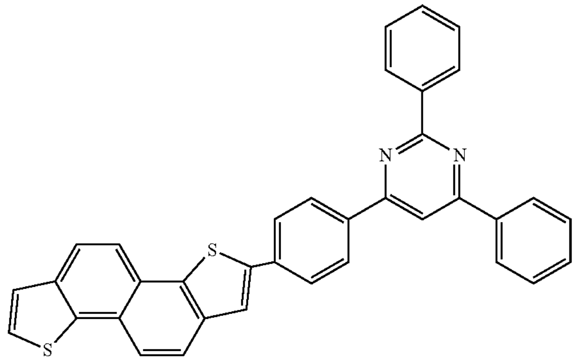
C40
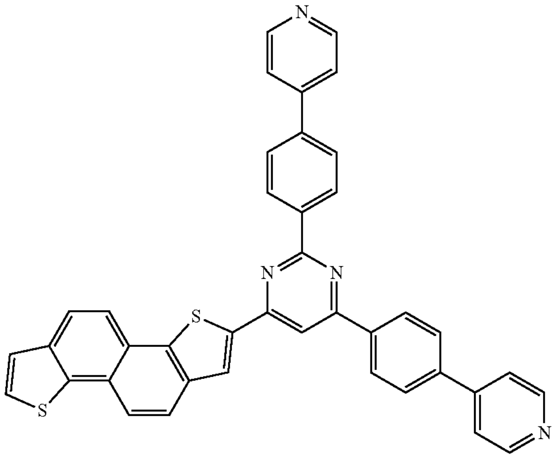

-continued
C41
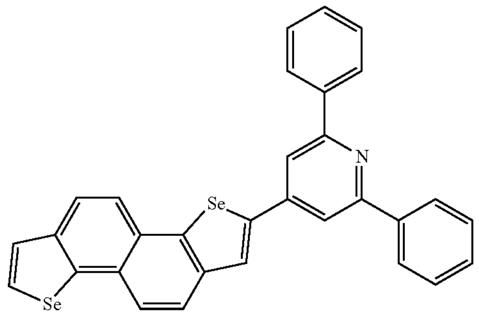
C42
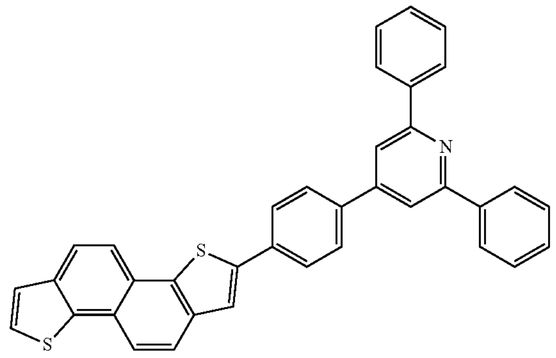
C43
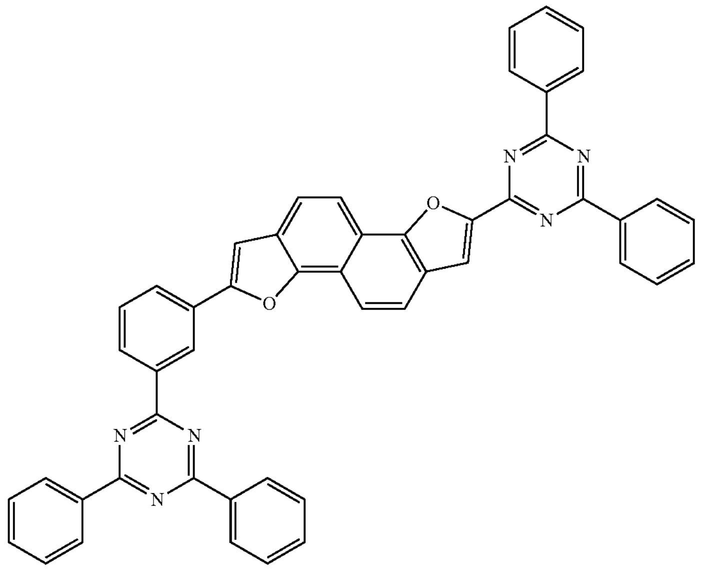
C44
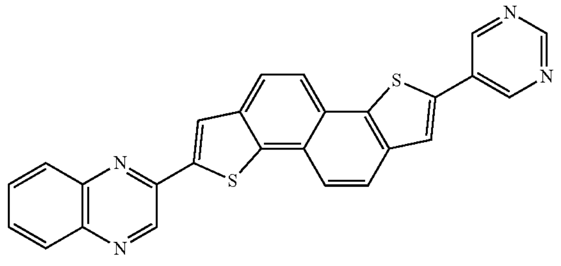
C45
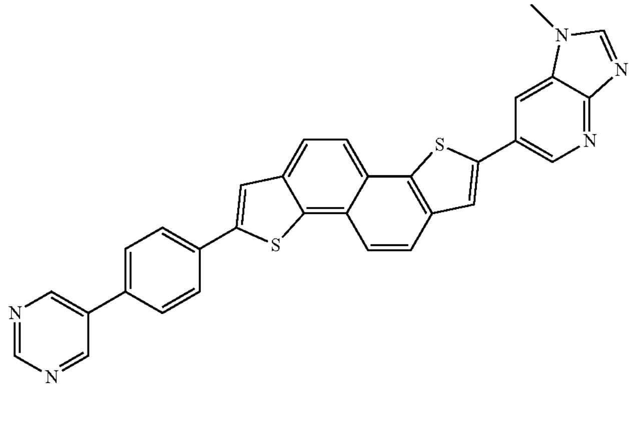

-continued
C46
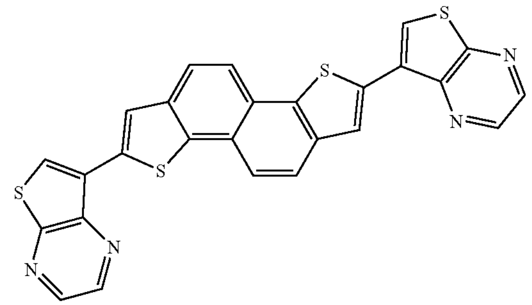
C47
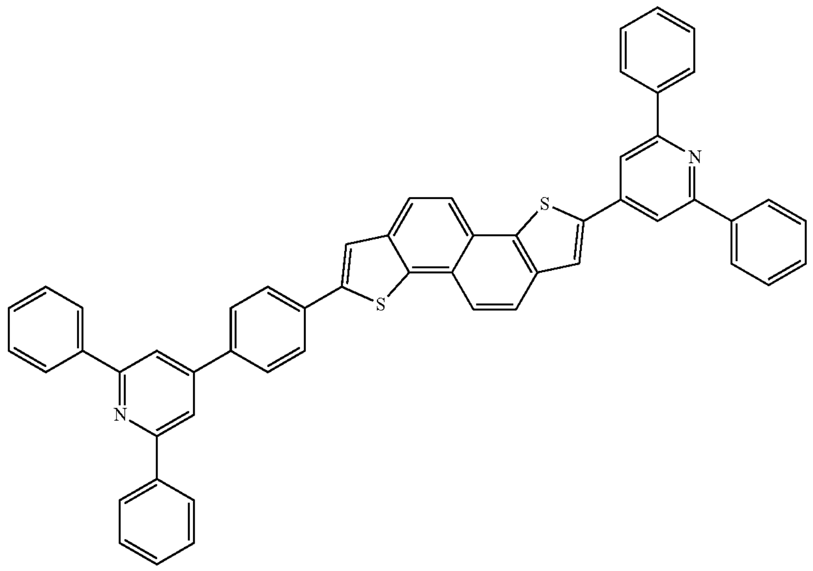
C48
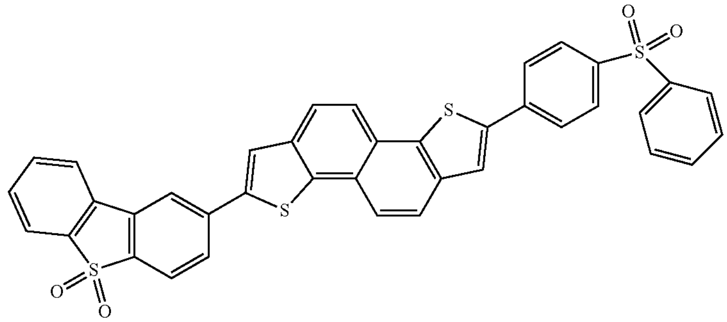

-continued
C49
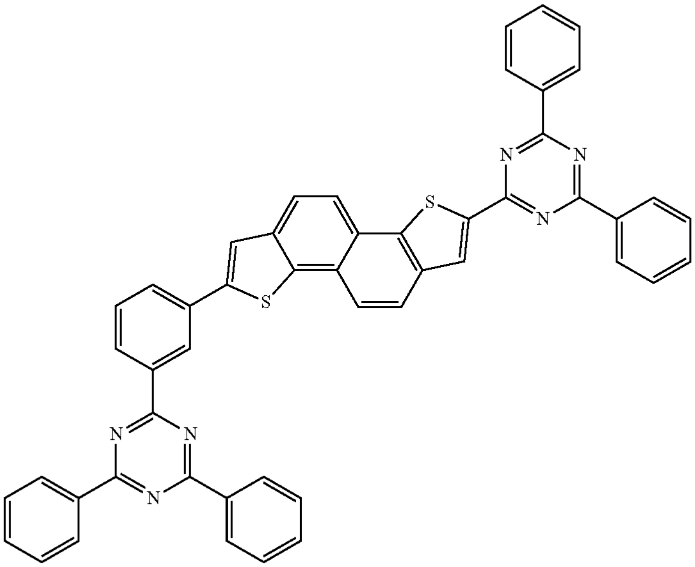
C50
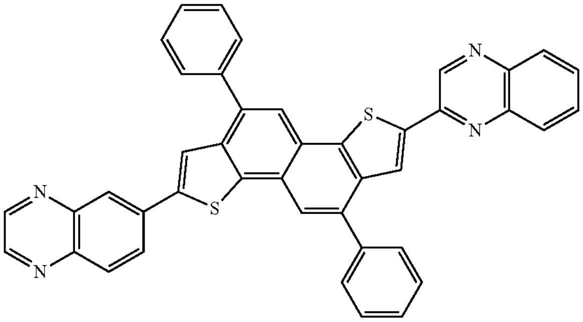
C51
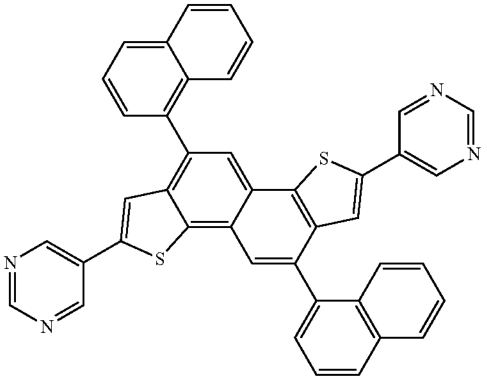
C52
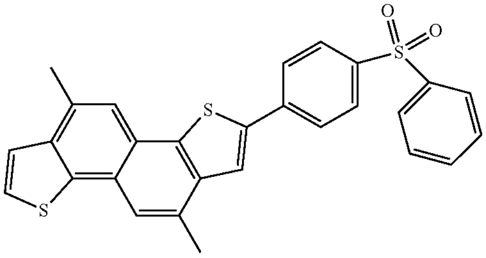
C53
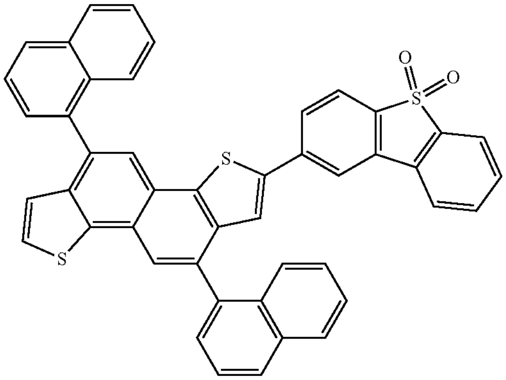

-continued

C54

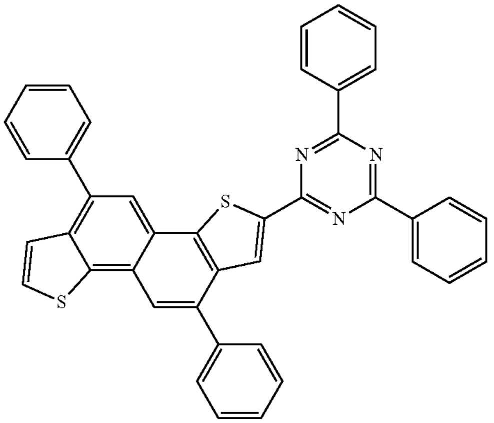

C55

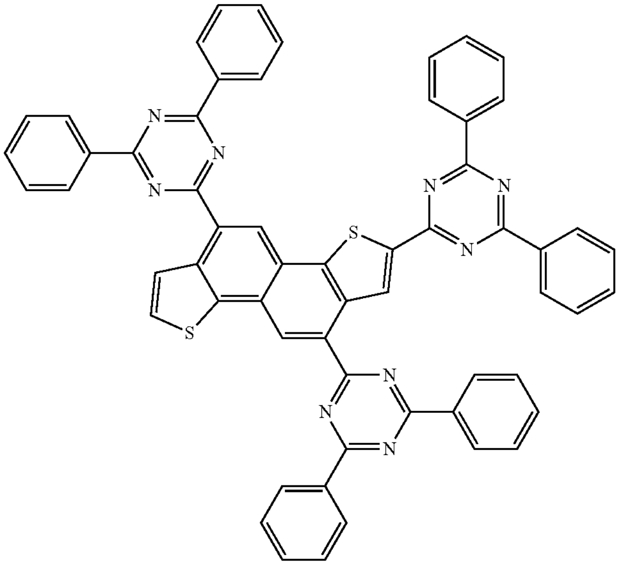

C56

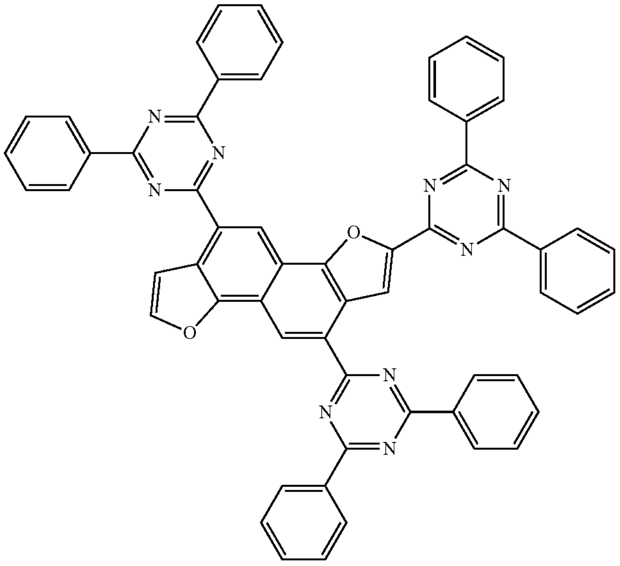

Detailed preparation for the organic material in the present invention could be clarified by exemplary embodiments, but the present invention is not limited to exemplary embodiments. EXAMPLE 1 to EXAMPLE 7 show the preparation for examples of the organic material in the present invention. EXAMPLE 8 show the fabrication of organic EL device and I-V-B, half-life time of organic EL device testing report.

Example 1

Synthesis of C4

Synthesis of 1,5-dichloro-2,6-dihydroxynaphthalene

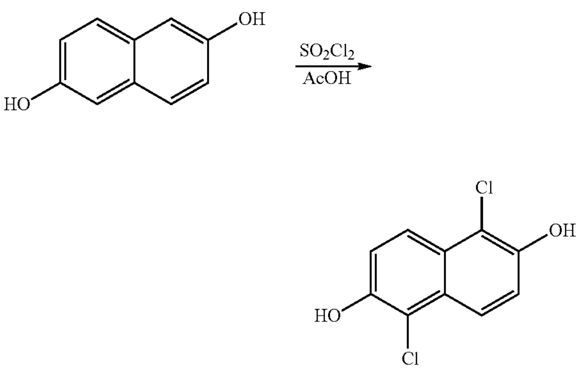

A mixture of 15 g (93 mmol) of 2,6-dihydroxynaphthalene, was dissolved in acetic acid (300 ml) under nitrogen, and then cool to 10° C., 15 ml (187 mmol) Sulfuryl chloride was then added, and the mixture was stirred 16 hr. After completion of the reaction, 400 ml of water was added, while stirring and the precipitated product was filtered off with suction. To give 18.2 g (yield 85%) as a white solid.

Synthesis of 1,5-dichloronaphthalene-2,6-diylbis (trifluoromethane sulfonate)

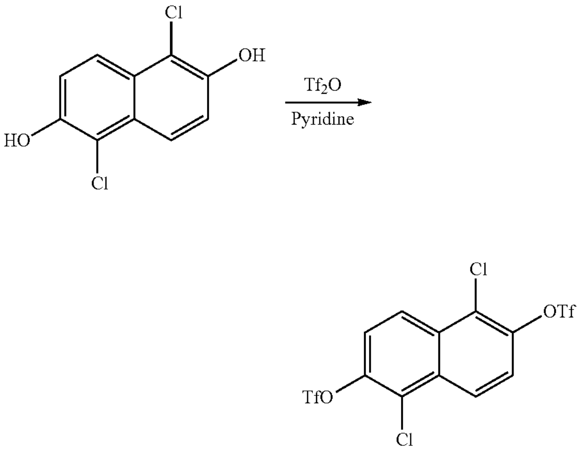

A mixture of 18.2 g (79 mmol) of 1,5-dichloro-2,6-dihydroxynaphthalene, 38.5 ml (480 mmol) of pyridine, and 300 ml dichloromethane was placed under nitrogen, 33.5 ml (199 mmol) Trifluoromethanesulfonic anhydride was then added, and the mixture was stirred two hour, water 50 ml and 1M HCl 50 ml were added to the mixture and the organic layer was separated and washed with dichloromethane. After drying over magnesium sulfate, the solvent was removed in vacuo. To give 37.7 g (yield 96%) of white product was recrystallized from hexane.

Synthesis of 1,5-Dichloro-2,6-bis(trimethylsilylethynyl)naphtha-alene

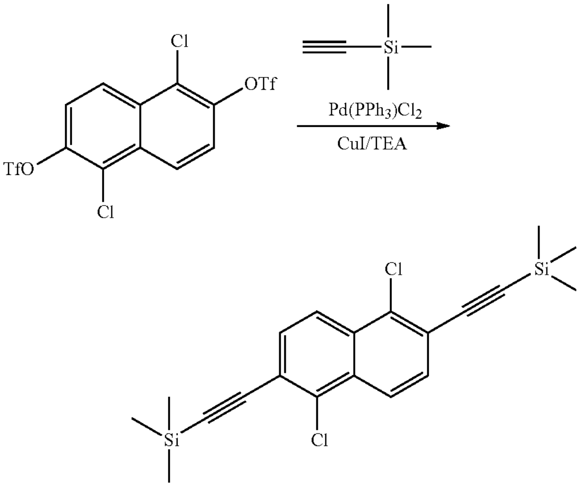

A mixture of 37.7 g (754 mmol) of 1,5-dichloro-2,6-bis (trifluoromethane sulfonyloxy)naphthalene, and 23.4 g (230 mmol)triethylamine in 300 ml THF were added 5.3 g (4.52 mmol) $Pd(PPh_3)_4$, 2.9 g (15.1 mmol) Copper(I)iodide, and 38 ml (263.9 mmol) Trimethylsilylacetylene was degassed and placed under nitrogen, and then heated at refluxed for 20 h. After finishing the reaction, the mixture was allowed to cool to room temperature. Water 80 ml and 1M HCl 80 ml were added. The resulting mixture was extracted with dichloromethane 400 ml. After drying over magnesium sulfate, the solvent was removed in vacuo. The residue was purified by column chromatography on silica(hexane-dichloromethane) to give product 7.9 g (yield 80%) as a light-yellow solid.

Synthesis of Naphtho[1,2-b:5,6-b']dithiophene

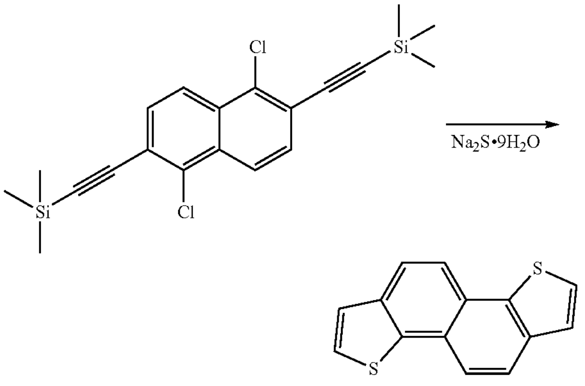

A mixture of 19.5 g (79 mmol) of Sodium sulfide nonahydrate, 470 ml of 1-Methyl-2-pyrrolidone, and stirred for 15 min at room temperature 7.9 g (19.8 mmol) 1,5-Dichloro-2,6-bis(trimethylsilylethynyl)naphthalene was then added, and then heated at 190° C. overnight. After finishing the reaction, the mixture was allowed to cool to room temperature. The mixture was poured into 800 ml saturated aqueous ammonium chloride solution. The resulting precipitate was collected by filtration. The residue was purified by column chromatography on silica(Hexane-EA) to give product 3.6 g (yield 74%) as a yellow solid.

Synthesis of 2,7-Dibromonaphtho[1,2-b:5,6-b']dithiophene

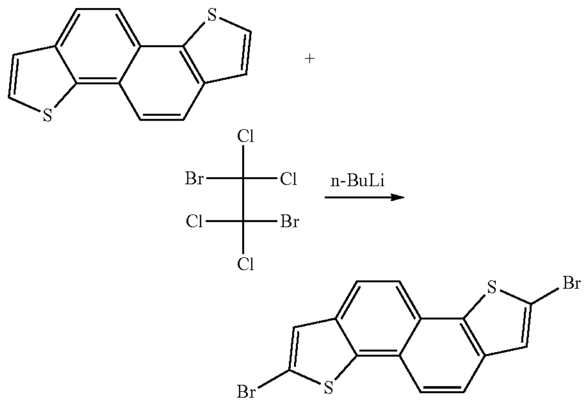

A mixture of 4.8 g (20 mmol) of Naphtho[1,2-b:5,6-b'] dithiophene, 300 ml of Dry THF, was placed under nitrogen, and then cool to −70° C., 32 ml (80 mmol) n-BuLi (2.5M in hexane) was then added, and the mixture was stirred 1 hr, 32.5 g (100 mmol) was then added, and the mixture was stirred 18 hr at 25° C., After finishing the reaction, The mixture was extracted with 500 ml dichloromethane and 200 ml water, the organic layer was dried with anhydrous magnesium sulfate, the solvent was removed and the residue was purified by column chromatography on silica(hexane) to give product 5 g (yield 63%) as an off-white solid.

Synthesis of C4

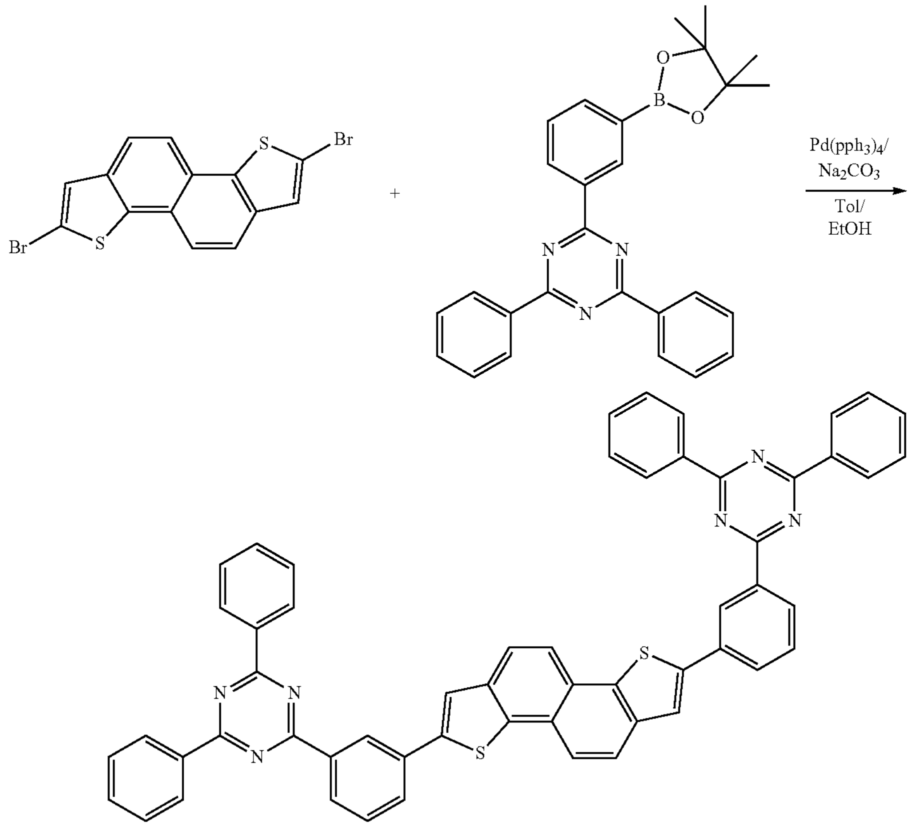

A mixture of 4 g (10 mmol) of 2,7-Dibromonaphtho[1,2-b:5,6-b']dithiophene, 9.6 g (22 mmol) of 2,4-diphenyl-6-(3-(4,4,5,5-tetramethyl-1,3,2-dioxaborolan-2-yl)phenyl)-1,3,5-triazine, 0.46 g (0.4 mmol) of tetrakis(triphenyl phosphine)palladium, 25 ml of 2M $Na_2CO_3$, 50 ml of EtOH and 150 ml toluene was degassed and placed under nitrogen, and then heated at 90° C. overnight. After finishing the reaction, the mixture was allowed to cool to room temperature. Then 100 ml of MeOH was added, while stirring and the precipitated product was filtered off with suction. To give 3.6 g (yield 43%) of off-white product which was recrystallized from toluene. MS (m/z, $FAB^+$): 855.4, $^1H$ NMR ($CDCl_3$, 400 MHz): chemical shift (ppm) 8.28~8.24 (m, 10H), 7.92 (d, 2H), 7.71~7.41 (m, 20H), 7.35 (s, 2H).

Example 2

Synthesis of C5

Synthesis of 2-Bromonaphtho[1,2-b:5,6-b']dithiophene

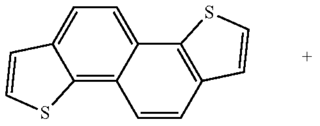

-continued

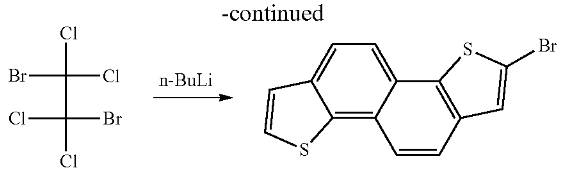

A mixture of 4.8 g (20 mmol) of Naphtho[1,2-b:5,6-b'] dithiophene, 300 ml of Dry THF, was placed under nitrogen, and then cool to −70° C., 12.8 ml (32 mmol) n-BuLi (2.5M in hexane) was then added, and the mixture was stirred 1 hr, 14.3 g (44 mmol) was then added, and the mixture was stirred 18 hr at 25° C., After finishing the reaction, the mixture was extracted with 500 ml dichloromethane and 200 ml water, the organic layer was dried with anhydrous magnesium sulfate, the solvent was removed and the residue was purified by column chromatography on silica(hexane) to give product 5 g (yield 78%) as an off-white solid.

Synthesis of C5

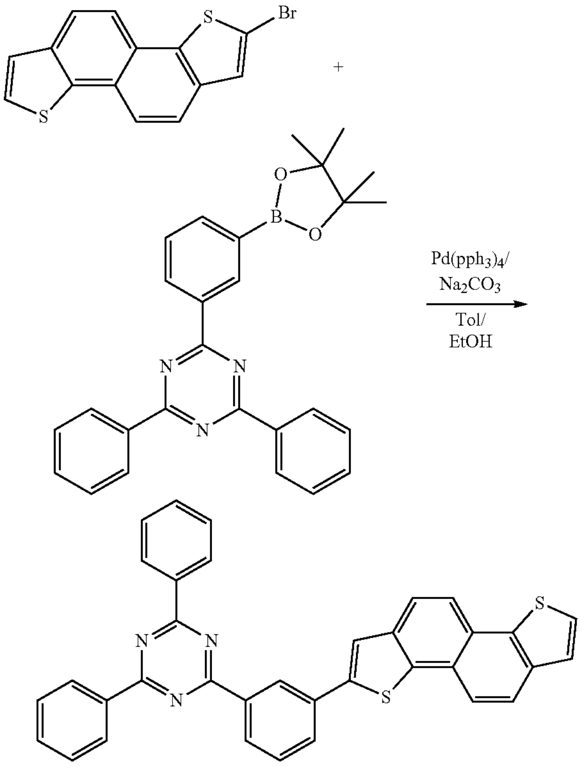

A mixture of 3.2 g (10 mmol) of 2-Bromonaphtho[1,2-b:5,6-b']dithiophene, 4.8 g (11 mmol) of 2,4-diphenyl-6-(3-(4,4,5,5-tetramethyl-1,3,2-dioxaborolan-2-yl)phenyl)-1,3,5-triazine, 0.23 g (0.2 mmol) of tetrakis(triphenyl phosphine) palladium, 20 ml of 2M $Na_2CO_3$, 40 ml of EtOH and 120 ml toluene was degassed and placed under nitrogen, and then heated at 90° C. overnight. After finishing the reaction, the mixture was allowed to cool to room temperature. Then 100 ml of MeOH was added, while stirring and the precipitated product was filtered off with suction. To give 2.8 g (yield 51%) of off-white product which was recrystallized from toluene. MS (m/z, $FAB^+$): 547.7 $^1H$ NMR ($CDCl_3$, 400 MHz): chemical shift (ppm) 8.28~8.24 (m, 5H), 7.92 (d, 2H), 7.71~7.41 (m, 13H), 7.33 (s, 1H).

Example 3

Synthesis of C9

Synthesis of 2-(4,4,5,5-tetramethyl-1,3,2-dioxaborolan-2-yl) naphtha[1,2-b:5,6-b']dithiophene

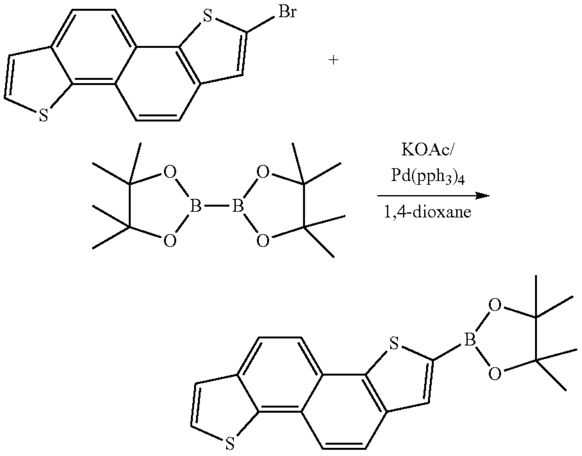

A mixture of 6.4 g (20 mmol) of 2-Bromonaphtho[1,2-b:5,6-b']dithiophene, 6.0 g (24 mmol) of bis(pinacolato) diboron, 0.46 g (0.4 mmol) of tetrakis(triphenylphosphine) palladium, 5.8 g (60 mmol) of potassium acetate, and 200 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica (hexane-dichloro methane) to give product 4.2 g (58%) as a light-yellow solid.

Synthesis of C9

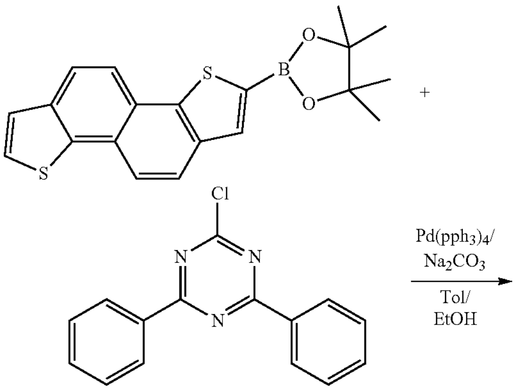

-continued

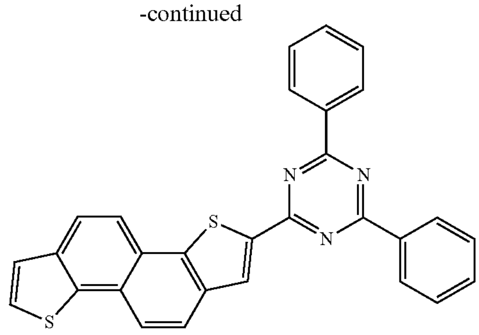

A mixture of 3.7 g (10 mmol) of 2-(4,4,5,5-tetramethyl-1,3,2-dioxaborolan-2-yl)-naphtho[1,2-b:5,6-b]dithiophene, 5.4 g (20 mmol) of 2-chloro-4,6-diphenyl-1,3,5-triazine, 0.22 g (0.2 mmol) of tetrakis(triphenylphosphine) palladium, 15 ml of 2M $Na_2CO_3$, 20 ml of EtOH and 40 ml toluene was degassed and placed under nitrogen, and then heated at 90° C. overnight. After finishing the reaction, the mixture was allowed to cool to room temperature. Then 100 ml of MeOH was added, while stirring and the precipitated product was filtered off with suction. To give 2.3 g (yield 49%) of yellow product which was recrystallized from toluene. MS (m/z, $FAB^+$): 471.6 $^1H$ NMR ($CDCl_3$, 400 MHz): chemical shift (ppm) 8.28 (d, 4H), 7.92 (d, 2H), 7.78 (d, 1H), 7.65~7.41 (m, 8H), 7.33 (s, 1H).

Example 4

Synthesis of C16

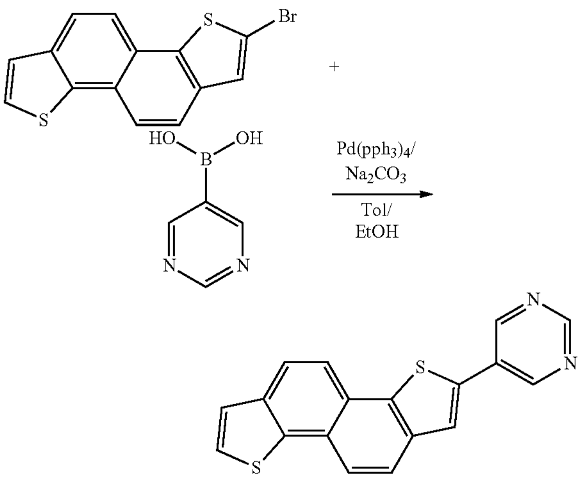

A mixture of 3.2 g (10 mmol) of 2-Bromonaphtho[1,2-b:5,6-b']dithiophene, 1.5 g (12 mmol) of 5-pyrimidylboronic acid, 0.23 g (0.2 mmol) of tetrakis (triphenylphosphine) palladium, 20 ml of 2M $Na_2CO_3$, 40 ml of EtOH and 120 ml toluene was degassed and placed under nitrogen, and then heated at 90° C. overnight. After finishing the reaction, the mixture was allowed to cool to room temperature. Than 100 ml of MeOH was added, while stirring and the precipitated product was filtered off with suction. To give 1.8 g (yield 56%) of off-white product which was purified by column chromatography on silica(EA-Hexane). MS (m/z, $FAB^+$): 318.4 $^1H$ NMR ($CDCl_3$, 400 MHz): chemical shift (ppm) 9.25 (s, 1H), 9.05 (s, 2H), 7.92 (d, 2H), 7.79~7.61 (m, 4H), 7.33 (s, 1H)

Example 5

Synthesis of C26

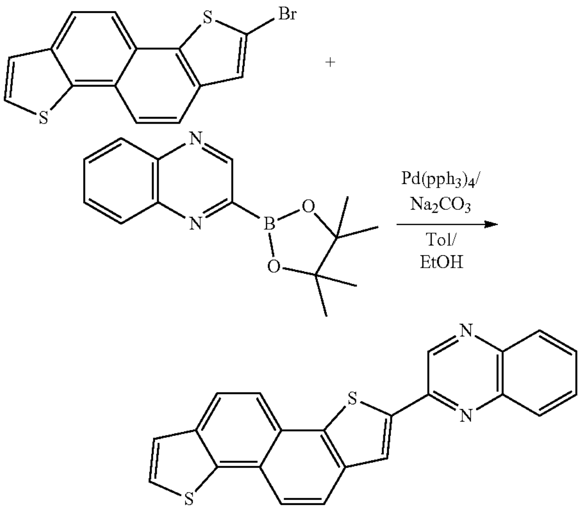

A mixture of 3.2 g (10 mmol) of 2-Bromonaphtho[1,2-b:5,6-b']dithiophene, 3.6 g (14 mmol) of 2-(4,4,5,5-tetramethyl-1,3,2-dioxaborolan-2-yl) quinoxaline, 0.23 g (0.2 mmol) of tetrakis(triphenylphosphine)palladium, 20 ml of 2M $Na_2CO_3$, 40 ml of EtOH and 120 ml toluene was degassed and placed under nitrogen, and then heated at 90° C. overnight. After finishing the reaction, the mixture was allowed to cool to room temperature. Than 100 ml of MeOH was added, while stirring and the precipitated product was filtered off with suction. To give 2.2 g (yield 61%) of off-white product which was purified by column chromatography on silica(EA-Hexane). MS (m/z, $FAB^+$): 368.5 $^1H$ NMR ($CDCl_3$, 400 MHz): chemical shift (ppm) 8.71 (s, 1H), 7.92 (d, 2H), 7.81 (d, 2H), 7.71~7.55 (m, 6H), 7.33 (s, 1H).

Example 6

Synthesis of C27

Synthesis of 2-Bromodibenzothiophene-S,S-dioxide

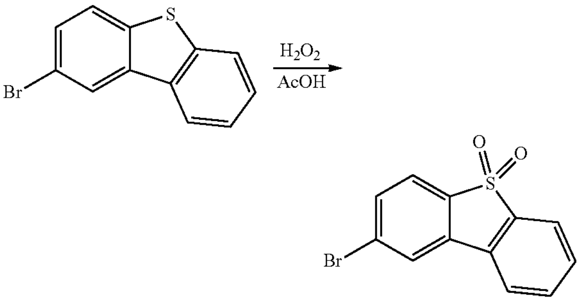

A mixture of 4.15 g (15.8 mmol) of 2-bromodibenzothiophene, 250 ml of acetic acid was degassed and placed under nitrogen then heated at 80° C. 30 min, 100 ml $H_2O_2$ was then added, and the mixture was stirred 2 hr at reflux, After finishing the reaction, the mixture was allowed to cool to room temperature. The precipitated product was filtered off with suction and wash with water. To give 4.0 g (yield 77%) of off-white product.

Synthesis of C27

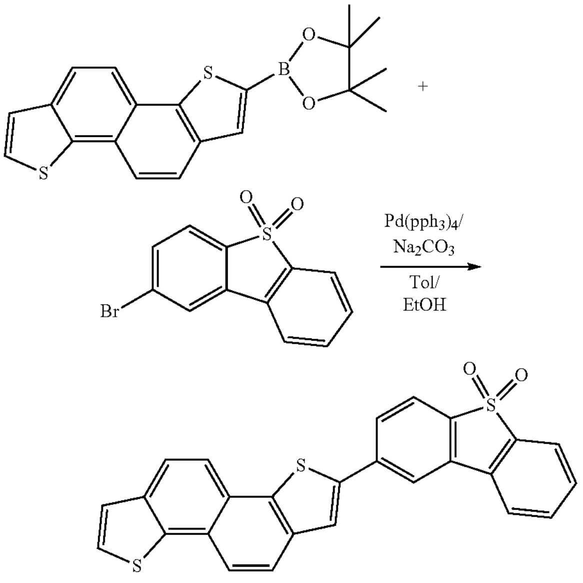

A mixture of 3.7 g (10 mmol) of 2-(4,4,5,5-tetramethyl-1,3,2-dioxaborolan-2-yl)-naphtho[1,2-b:5,6-b']dithiophene, 3.4 g (13 mmol) of 2-bromo-dibenzo[b,d]thiophene, 0.22 g (0.2 mmol) of tetrakis(triphenylphosphine) palladium, 15 ml of 2M $Na_2CO_3$, 20 ml of EtOH and 40 ml toluene was degassed and placed under nitrogen, and then heated at 90° C. overnight. After finishing the reaction, the mixture was allowed to cool to room temperature. Then 100 ml of MeOH was added, while stirring and the precipitated product was filtered off with suction. To give 2.5 g (yield 59%) of off-white product was purified by column chromatography on silica(EA-DCM). MS (m/z, $FAB^+$): 454.6 $^1H$ NMR ($CDCl_3$, 400 MHz): chemical shift (ppm) 8.00~7.85 (m, 7H), 7.75 (d, 1H), 7.66~7.45 (m, 5H), 7.33 (s, 1H).

Example 7

Synthesis of C28

Synthesis of 4-Bromophenyl sulfone

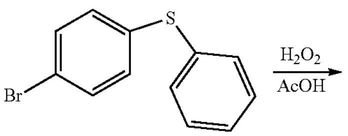

-continued

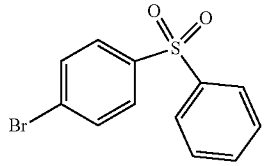

A mixture of 4.15 g (15.8 mmol) of 4-Bromodiphenyl sulfide, 250 ml of acetic acid was degassed and placed under nitrogen then heated at 80° C. 30 min, 100 ml $H_2O_2$ was then added, and the mixture was stirred 2 hr at reflux, After finishing the reaction, the mixture was allowed to cool to room temperature. The precipitated product was filtered off with suction and wash with water. To give 3.6 g (yield 70%) of off-white product.

Synthesis of C28

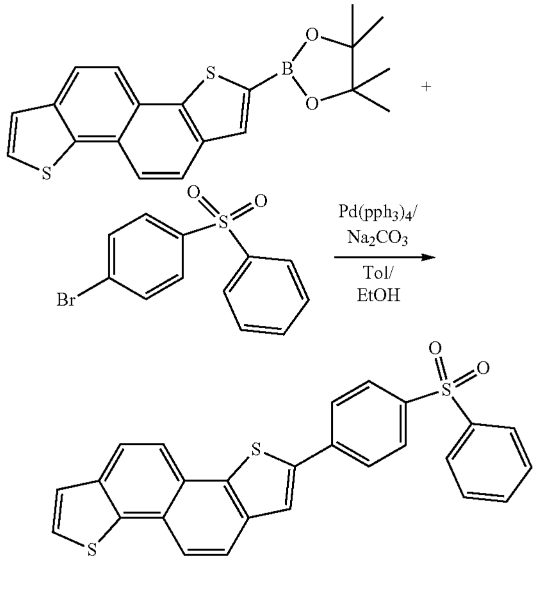

A mixture of 3.7 g (10 mmol) of 2-(4,4,5,5-tetramethyl-1,3,2-dioxaborolan-2-yl)-naphtho[1,2-b: 5,6-b']dithiophene, 3.2 g (12 mmol) of 1-bromo-4-(phenylsulfonyl)benzene, 0.22 g (0.2 mmol) of tetrakis(triphenylphosphine) palladium, 15 ml of 2M $Na_2CO_3$, 20 ml of EtOH and 40 ml toluene was degassed and placed under nitrogen, and then heated at 90° C. overnight. After finishing the reaction, the mixture was allowed to cool to room temperature. Than 200 ml of MeOH was added, while stirring and the precipitated product was filter off with suction. To give 2.4 g (yield 56%) of off-white product which was purified by column chromatography on silica(EA-DCM). MS (m/z, $FAB^+$): 456.6 $^1H$ NMR ($CDCl_3$, 400 MHz): chemical shift (ppm) 8.05~7.86 (m, 8H), 7.78~7.50 (m, 7H), 7.33 (s, 1H).

General Method of Producing Organic EL Device

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrate are under clean room (class 100).

These organic layers are applied onto the ITO substrate in order by vapor deposition in a high-vacuum unit (10 Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino[2,3-f:2,3-]quinoxaline-2,3,6,7,10,11-hexacarbonitrile (HAT-CN) is used as hole injection layer in this organic EL device, and N4,N4'-di(biphenyl-4-yl)-N4,N4'-diphenylbiphenyl-4,4'-diamine (HT1) is used as the hole transporting layer, N-(biphenyl-4-yl)-9,9-dimethyl-N-(4'-phenyl biphenyl-4-yl)-9H-fluoren-2-amine (EB2) is used as electron blocking layer, H1 used as phosphorescent host and delayed fluorescence host for comparable or standard with the present invention. The chemical structure shown below:

HAT-CN

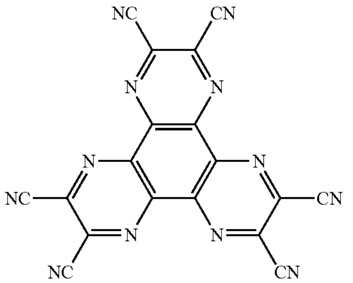

HT1

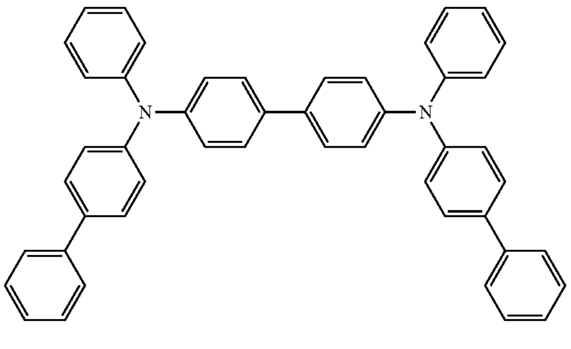

-continued

EB2

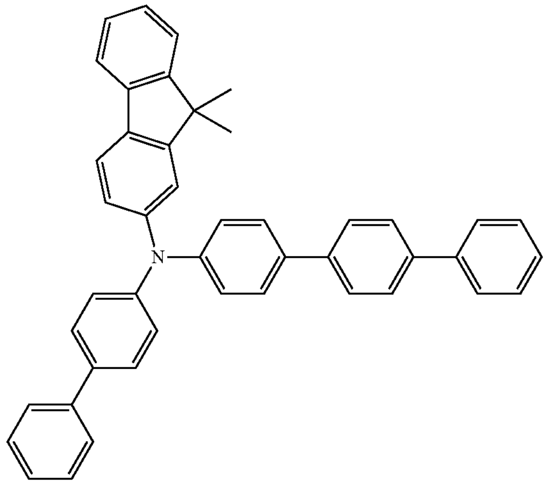

H1

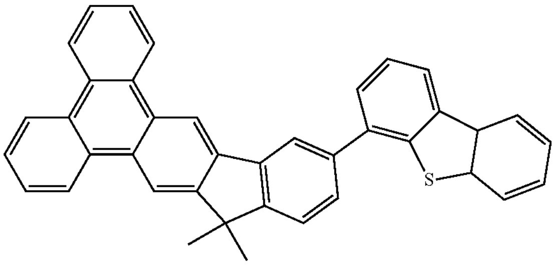

The following organic material Examples prepared in the present invention can be verified and used as delayed fluorescence dopant, phosphorescence host, hole blocking material or electron transporting material by organic EL device.

C4

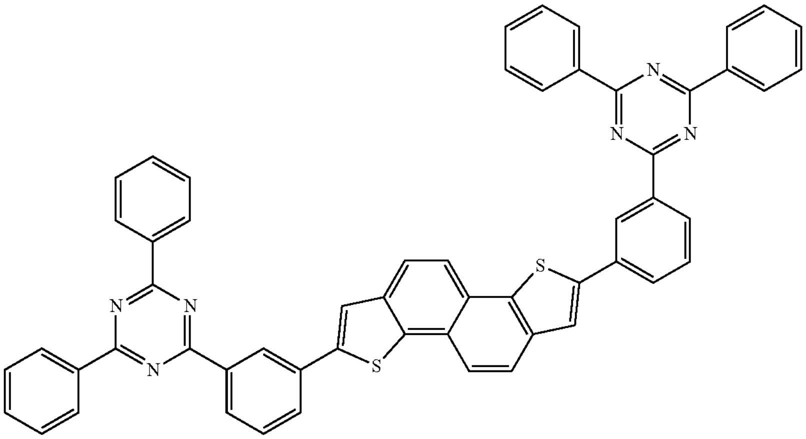

-continued

C5

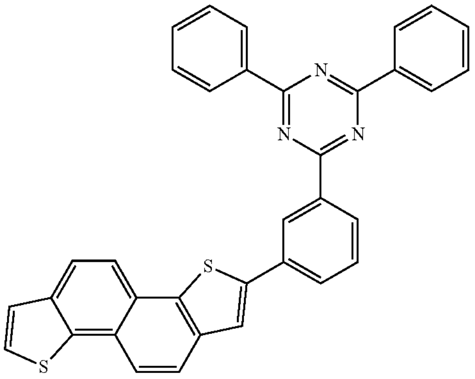

C9

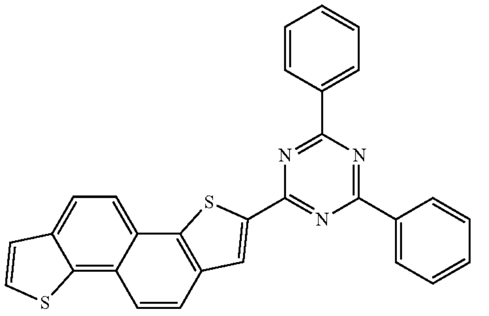

C16

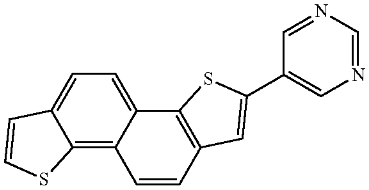

C26

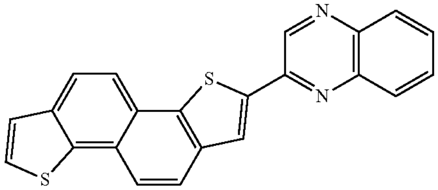

C27

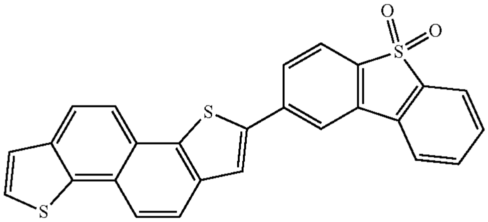

C28

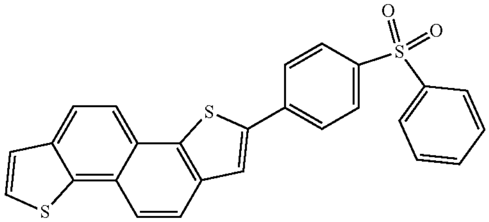

Organic iridium complexes are widely used as phosphorescent dopant for light emitting layer, Ir(ppy)$_3$ are widely used for phosphorescent green dopant of light emitting layer for organic EL device.

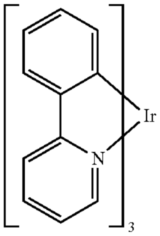

Ir(ppy)$_3$ 2,2',2"-(1,3,5-Benzinetriyl)-tris(1-phenyl-1-H-benzimidazole) (TPBi) and HB3 (see the following chemical structure) is used as hole blocking material (HBM) and 2-(10,10-dimethyl-10 OH-indeno[2,1-b]triphenylen-12-yl)-4,6-diphenyl-1,3,5-triazine (ET2) is used as electron transporting material to co-deposit with 8-hydroxyquinolato-lithium (LiQ) in organic EL device. The prior art of other OLED materials for producing standard organic EL device control and comparable material in this invention shown its chemical structure as follows TPBi

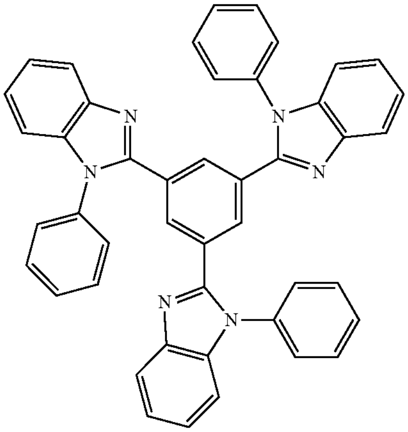

ET2

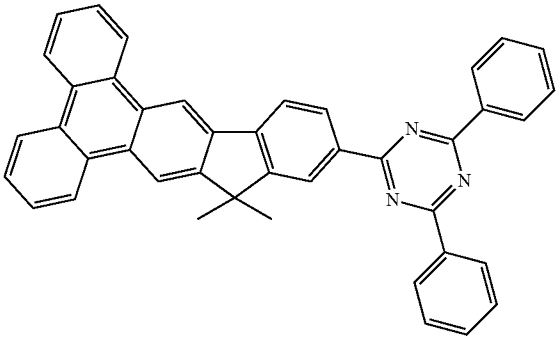

-continued

LiQ

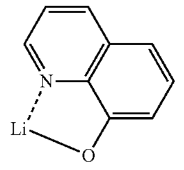

HB3

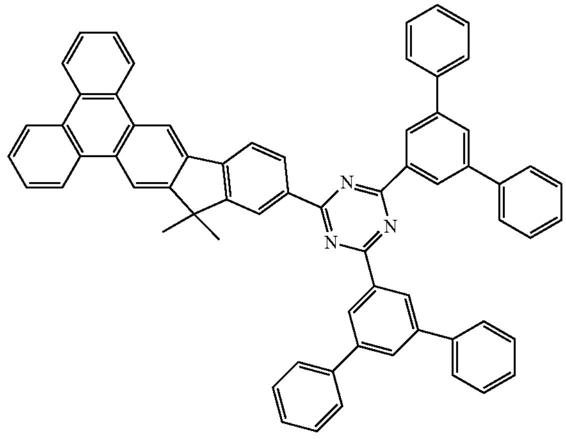

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$.

On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature (about 25° C.) and under atmospheric pressure.

Example 8

Using a procedure analogous to the above mentioned general method, organic EL device having the following device structure was produced (See FIG. 1). Device: ITO/HAT-CN (20 nm)/HT1 (110 nm)/EB2 (5 nm)/Host+dopant (30 nm)/HBM (10 nm)/ETM doped 40% LiQ (35 nm)/LiQ (1 nm)/Al (160 nm). The I-V-B (at 1000 nits) of organic EL device testing report as Table 1.

TABLE 1

| Dopant (%) | Host | HBM | ETM | Voltage (V) | Efficiency (cd/A) |
|---|---|---|---|---|---|
| C4(35%) | H1 | TPBi | ET2 | 6.2 | 15 |
| C5(35%) | H1 | TPBi | ET2 | 6.8 | 13 |
| C4(35%) | H1 | HB3 | ET2 | 6.5 | 8 |
| C16(35%) | H1 | HB3 | ET2 | 7.5 | 6 |

TABLE 1-continued

| Dopant (%) | Host | HBM | ETM | Voltage (V) | Efficiency (cd/A) |
|---|---|---|---|---|---|
| C26(35%) | H1 | HB3 | ET2 | 7.8 | 16 |
| C27(35%) | H1 | HB3 | ET2 | 5.8 | 21 |
| C28(35%) | H1 | HB3 | ET2 | 5.5 | 23 |
| $Ir(ppy)_3$(8%) | C4 | HB3 | ET2 | 5.3 | 26 |
| $Ir(ppy)_3$(8%) | H1 | C5 | ET2 | 5.5 | 22 |
| $Ir(ppy)_3$(8%) | H1 | HB3 | C5 | 4.0 | 36 |
| $Ir(ppy)_3$(8%) | H1 | HB3 | C26 | 4.0 | 38 |
| $Ir(ppy)_3$(8%) | H1 | HB3 | ET2 | 3.5 | 32 |

In the above preferred embodiments for organic EL device testing report (see Table 1), we show that the organic material with a general formula (I) or formula (2) used as light emitting host of emitting layer, and/or an electron transporting layer, and/or a hole blocking layer, and/or a delayed fluorescence (TADF) material of emitting layer for organic EL device in the present invention display good performance.

To sum up, the present invention discloses an organic material which can be used as phosphorescent light emitting host of emitting layer, and/or an electron transporting layer, and/or a hole blocking layer, and/or a delayed fluorescence material of emitting layer for organic EL device The mentioned the organic material represented by the following formula (1) or formula (2)

formula(1)

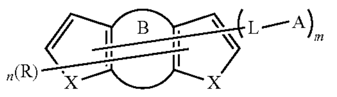

formula(2)

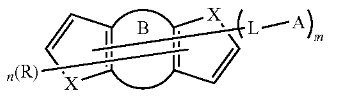

wherein A is an electron acceptor moiety represented from formula (3) to formula (12)

formula(3)

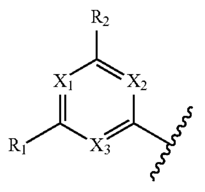

formula(4)

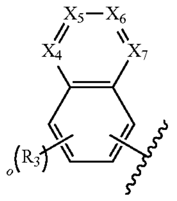

-continued formula(5)

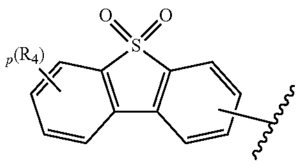

formula(6)

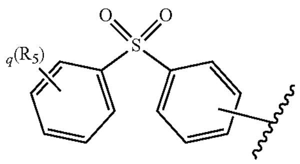

formula(7)

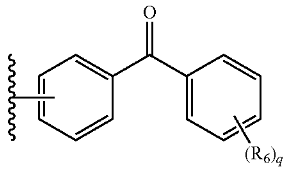

formula(8)

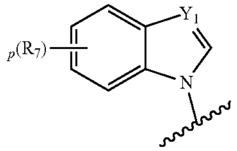

formula(9)

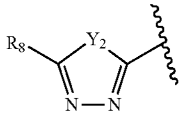

formula(10)

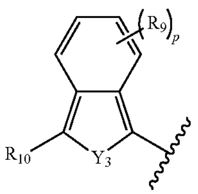

-continued formula(11)

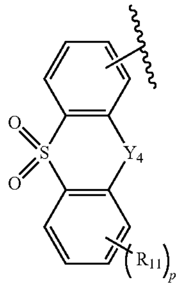

formula(12)

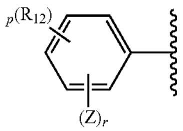

L represents a single bond or a substituted or unsubstituted divalent arylene group having 6 to 30 ring carbon atoms, m represents an integer of 1 to 4, n represents an integer of 1 to 3, X independently represents an oxygen atom, a sulfur atom and a selenium atom, B represents a fused ring hydrocarbon units with two or three rings; o represents an integer of 0 to 3, p represents an integer of 0 to 4, q represents an integer of 0 to 5, r represents an integer of 1 to 5, $Y_1$ to $Y_4$ is a divalent bridge selected from the atom or group consisting from O, S, $C(R_{13})(R_{14})$, $NR_{15}$, and $Si(R_{16})(R_{17})$; $X_1$ to $X_7$ represent a nitrogen atom or $C(R_8)$, and each R-represents a hydrogen, a phenyl, a substituted or unsubstituted alkyl group having 1 to 30 carbon atoms, and a substituted or unsubstituted aryl group having 6 to 30 carbon atoms; Z represents a cyano group, R and $R_1$ to $R_{17}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:

1. An organic material is one of the following:

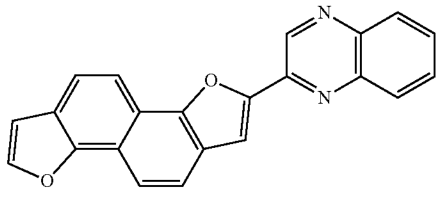

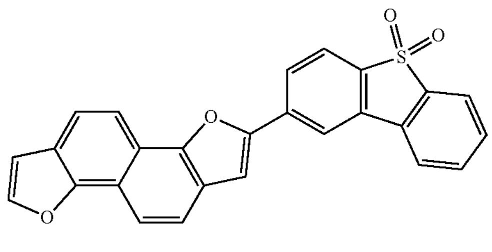

-continued
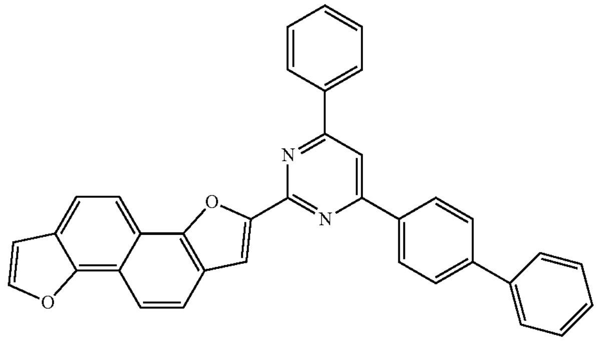
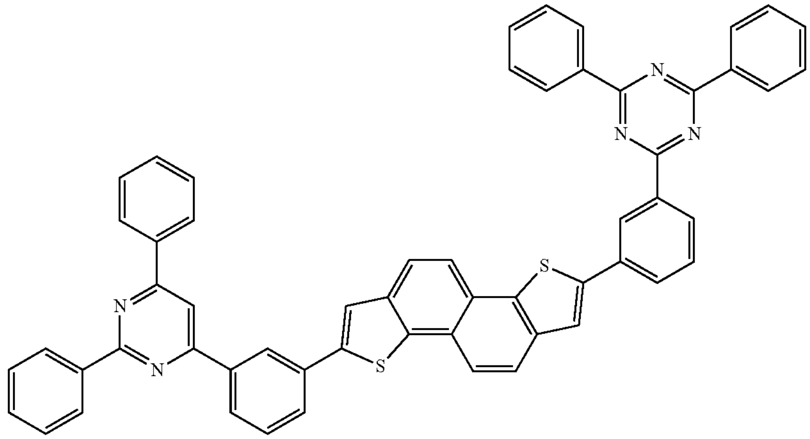
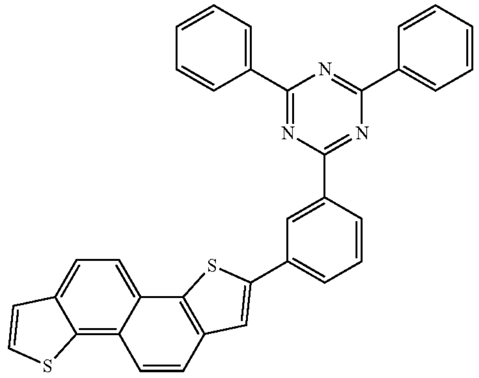
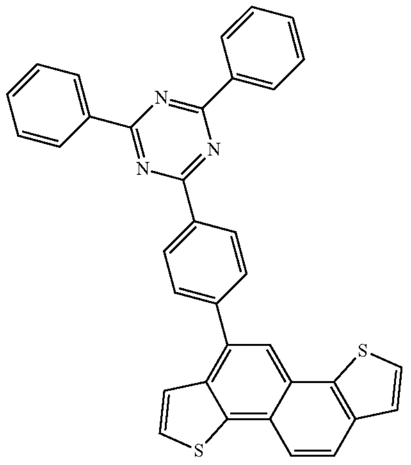
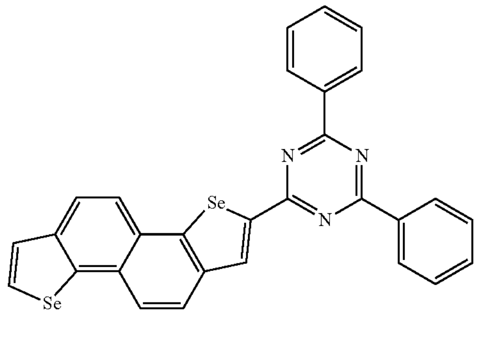
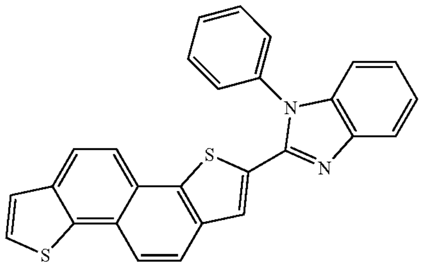

-continued
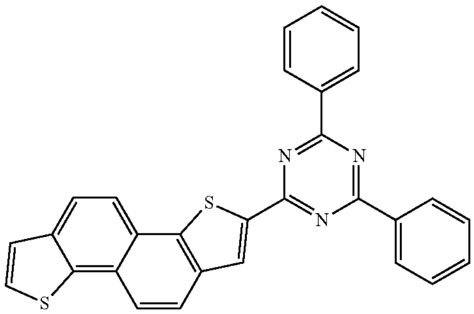
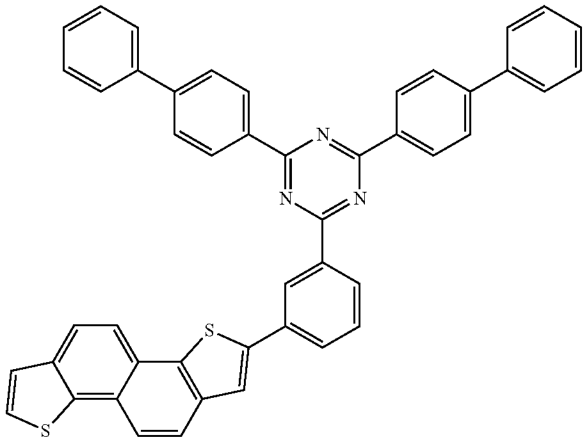
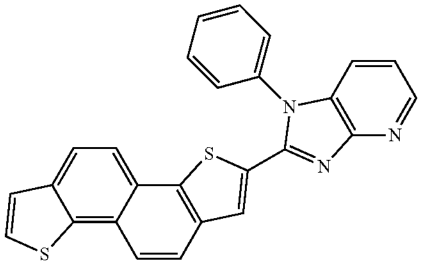
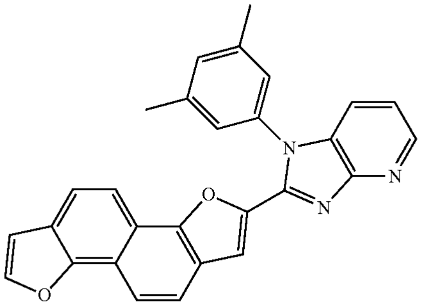
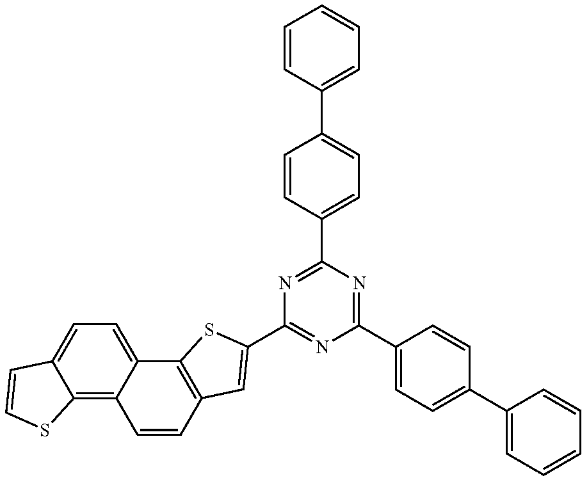
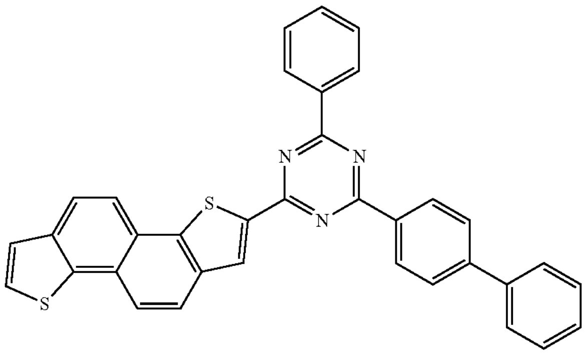

-continued
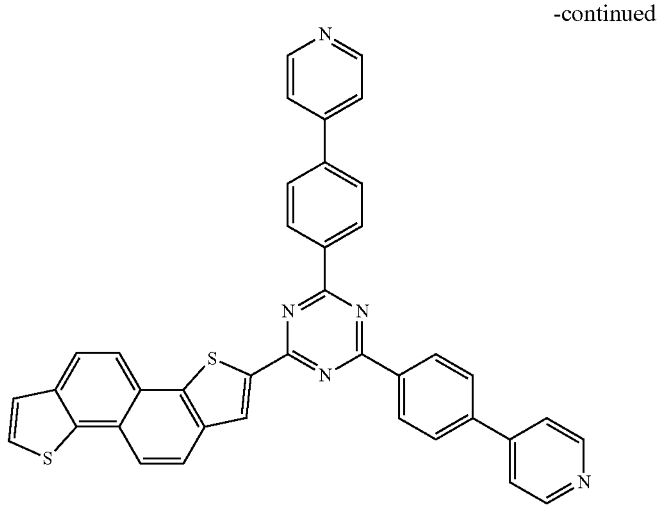
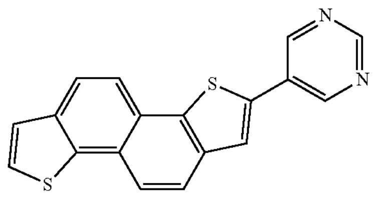
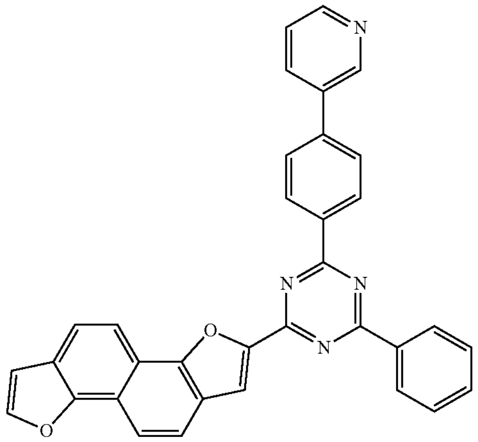
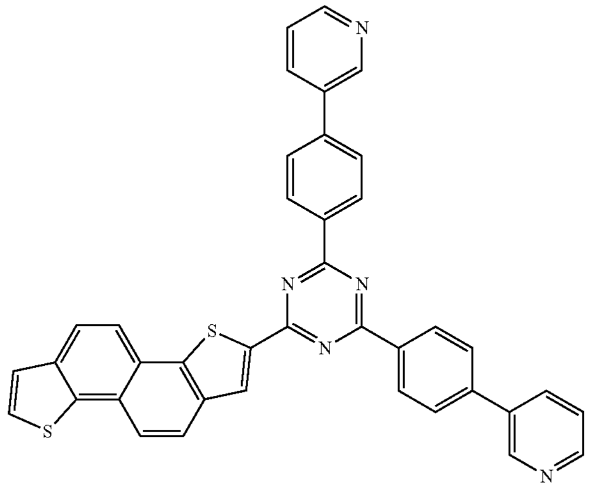
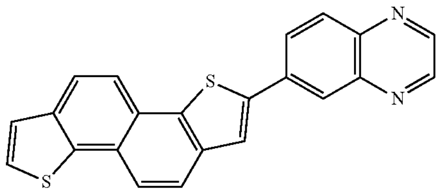
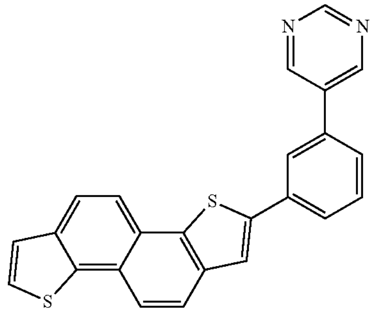
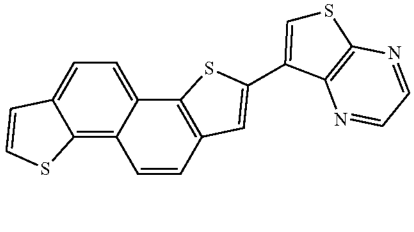

-continued
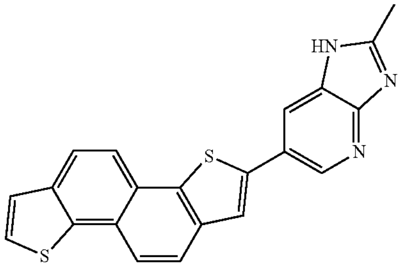
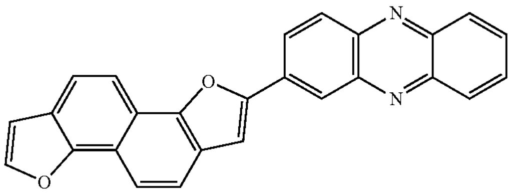
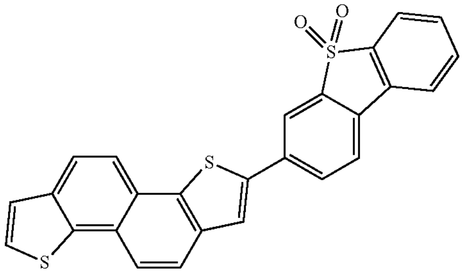
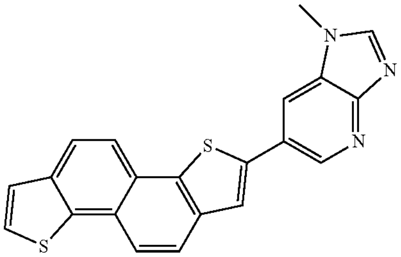
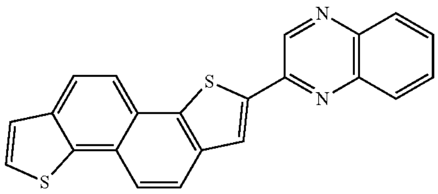
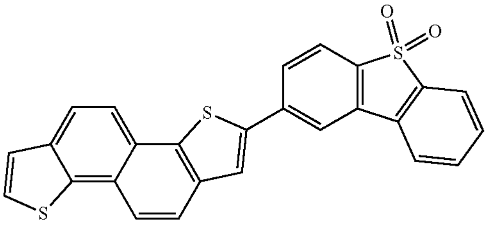
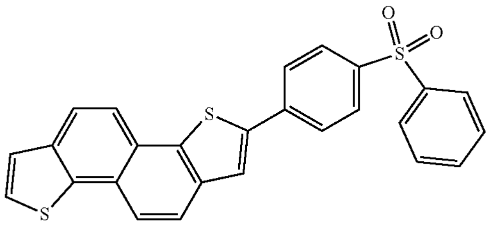
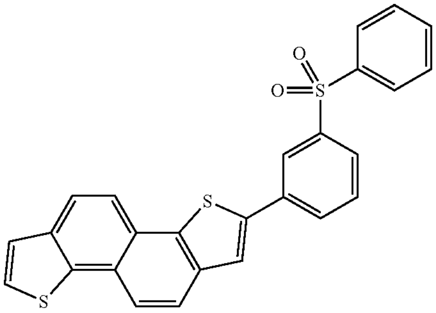
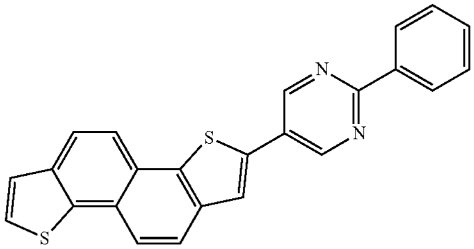
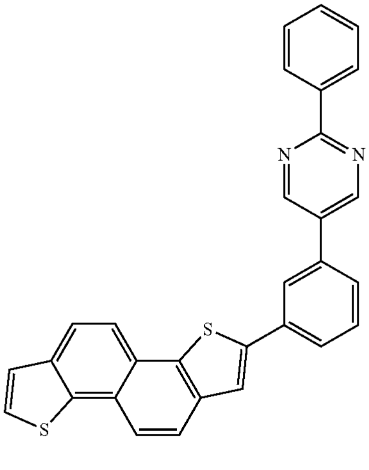

-continued
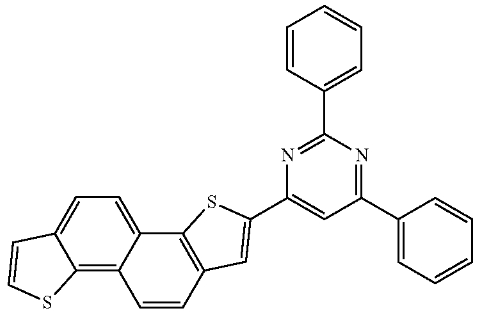
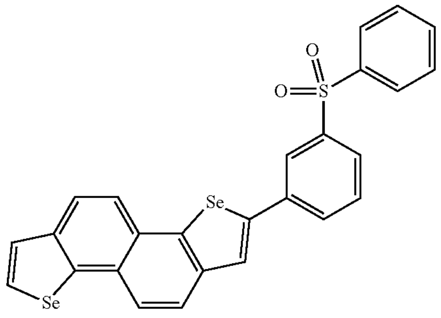
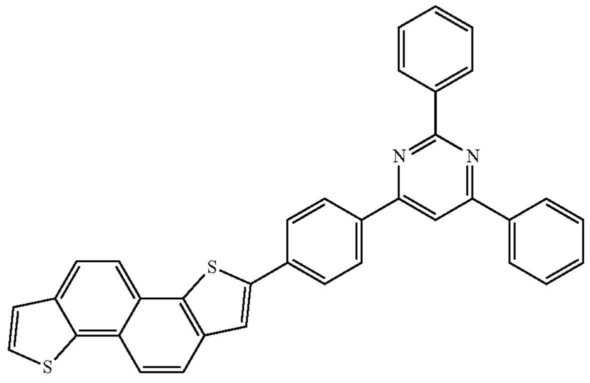
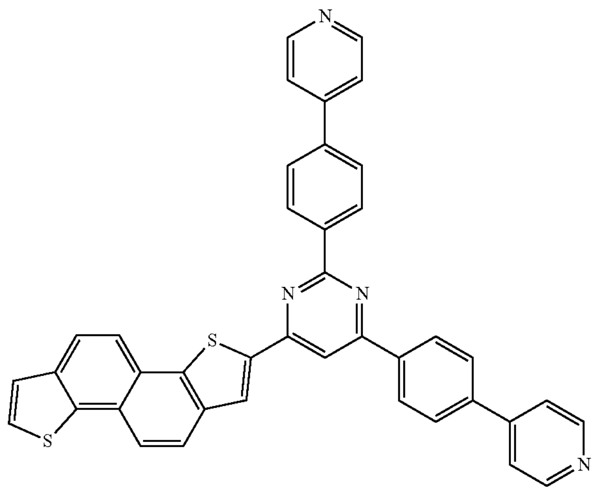
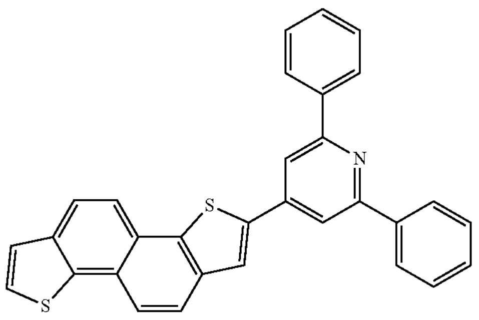
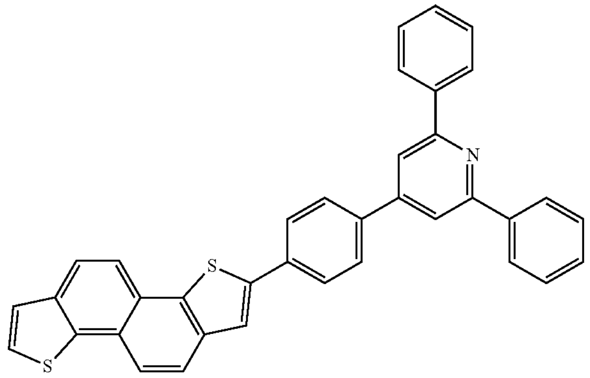
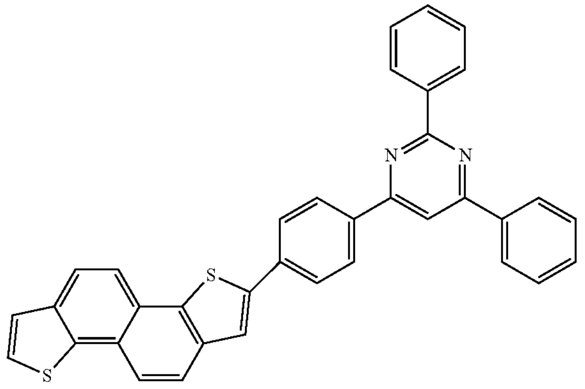

-continued
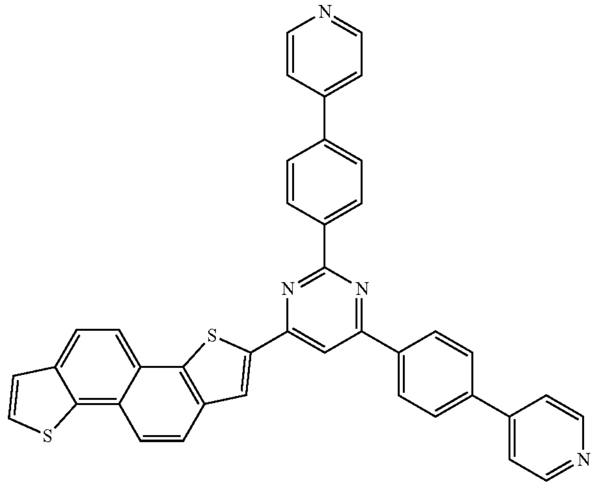
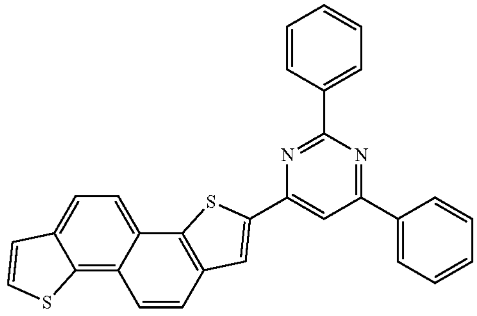
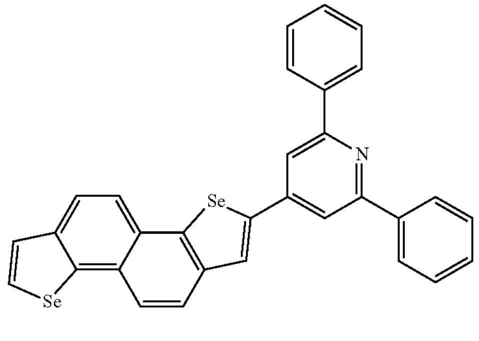
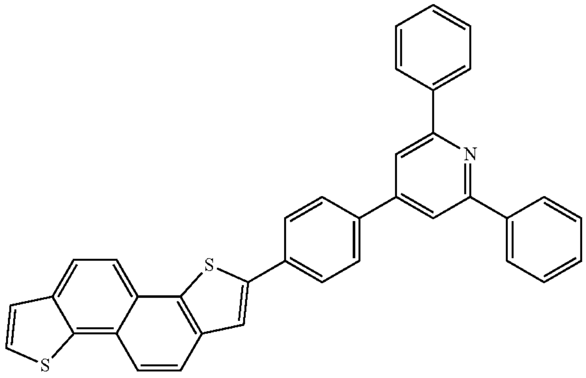
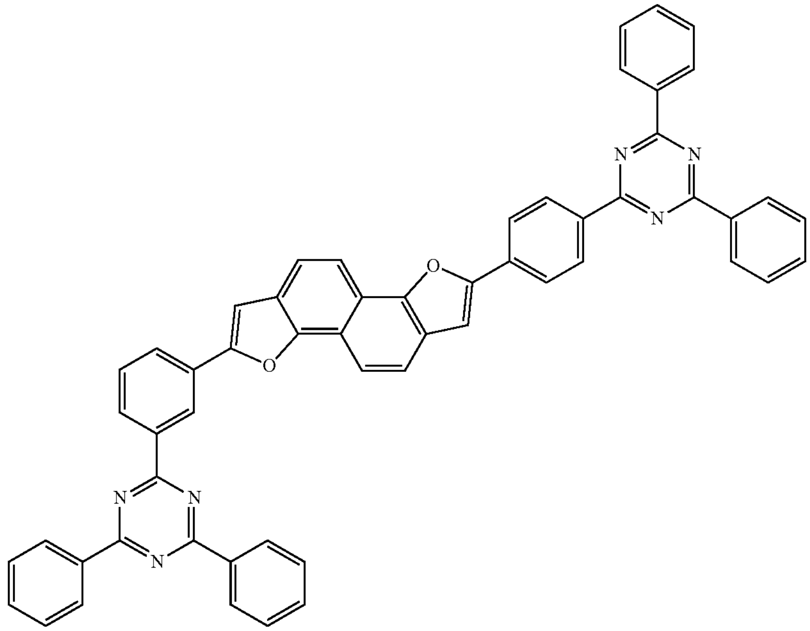

-continued
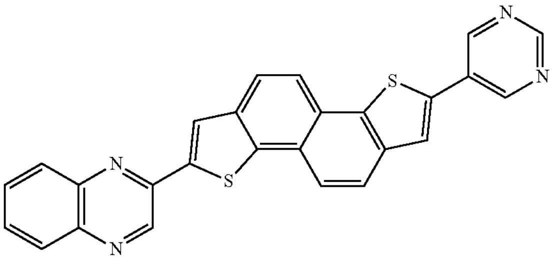
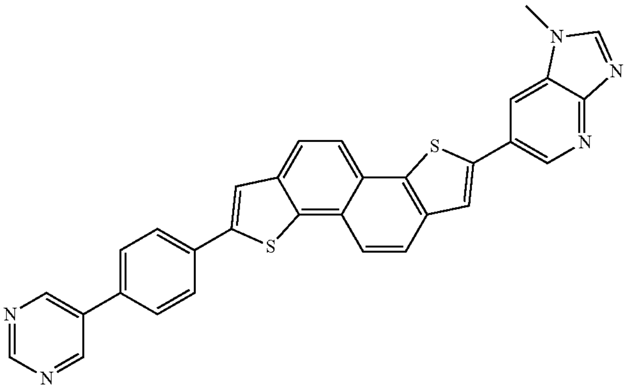
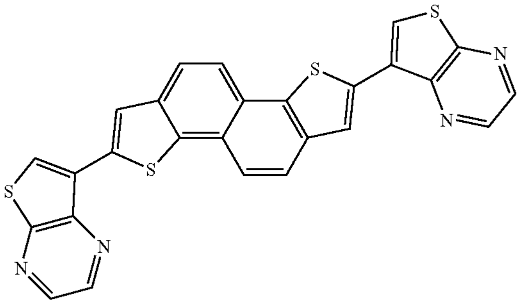
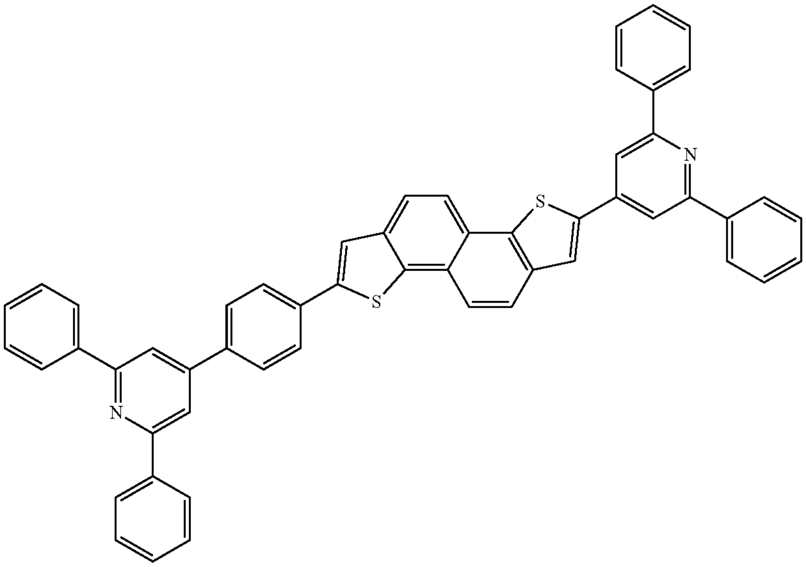

-continued
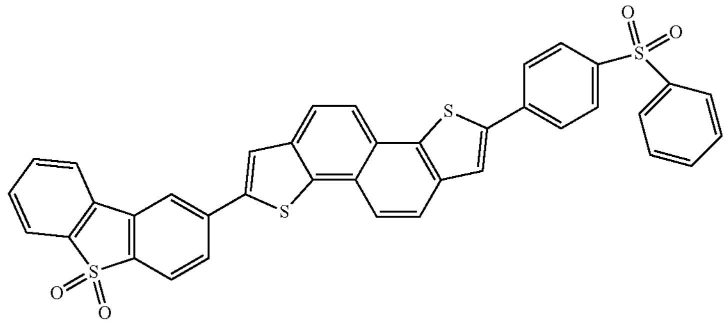
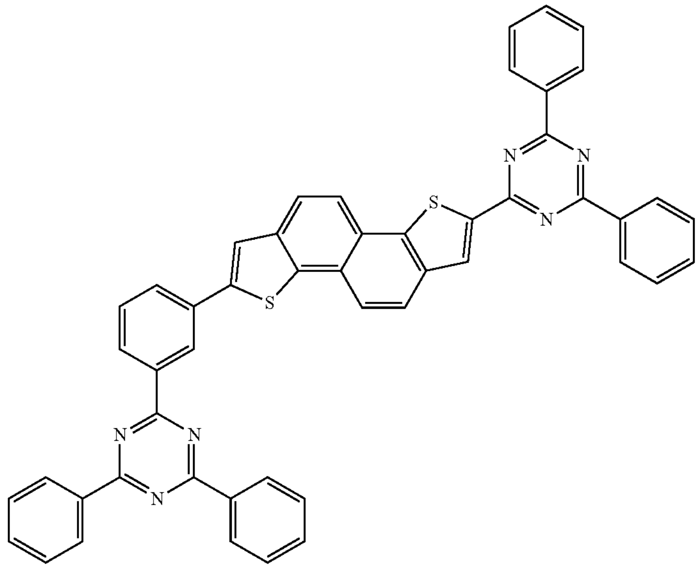
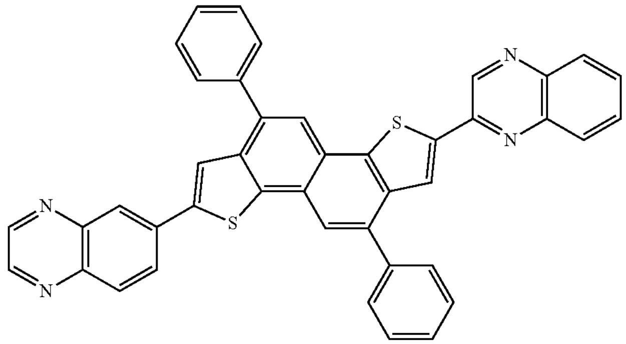
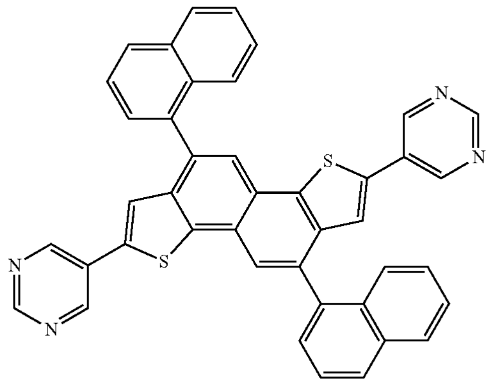
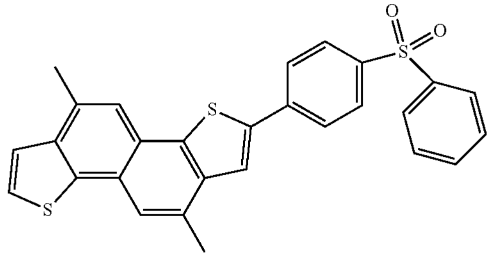
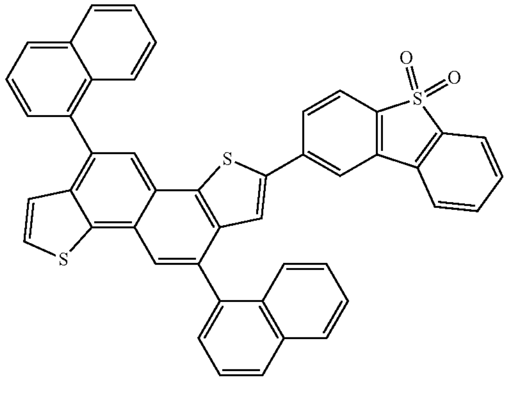

-continued

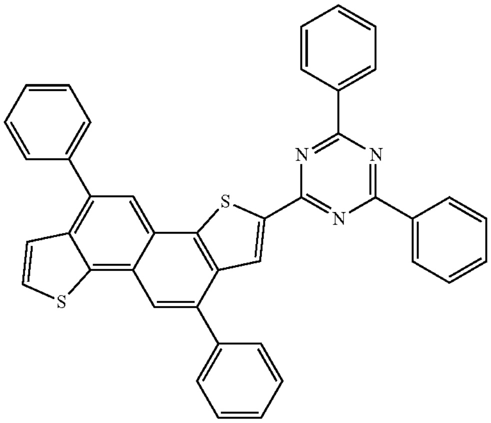

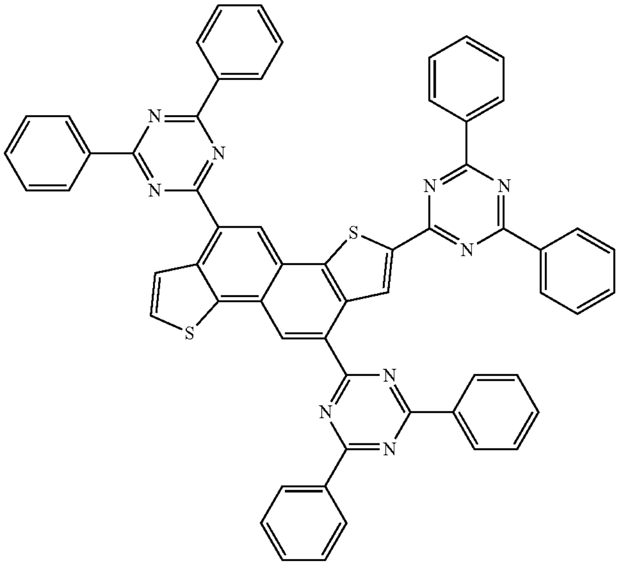

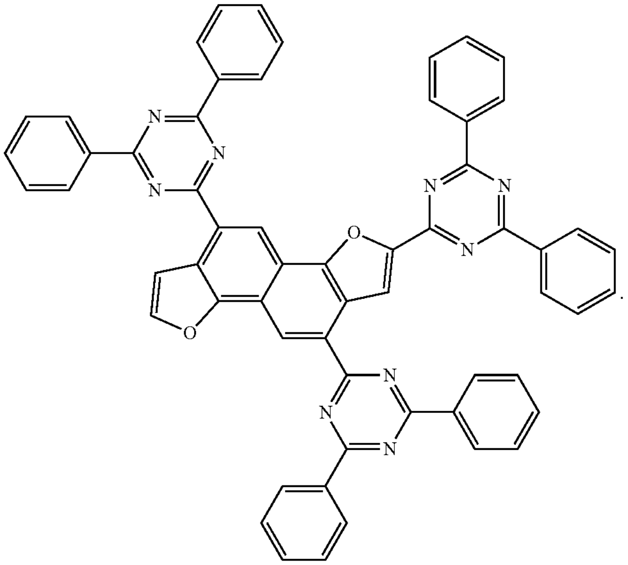

2. An organic electroluminescence device comprises a pair of electrodes consisting of a cathode and an anode, and between the pairs of electrodes comprise at least a light emitting layer, and one or more layers of organic thin film layer, wherein the light emitting layer or organic thin film layer comprises the organic material according to claim 1.

3. The organic electroluminescence device according to claim 2, wherein a difference between a singlet energy of the organic material and a triplet energy of the organic material is less than 0.25 eV.

4. The organic electroluminescence device according to claim 2, wherein the organic material is a delayed fluorescence compound.

5. The organic electroluminescence device according to claim 2, wherein the organic material is a delayed fluorescence host material.

6. The organic electroluminescence device according to claim 2, wherein the light emitting layer comprises a dopant material.

7. The organic electroluminescence device according to claim 2, wherein the light emitting layer comprises a host material.

8. The organic electroluminescence device according to claim 2, wherein the organic material is a phosphorescent host material.

9. The organic electroluminescence device according to claim 2, wherein the organic material is a hole blocking material.

10. The organic electroluminescence device according to claim 2, wherein the organic material is an electron transporting layer (ETL) material.

11. The organic electroluminescence device according to claim 2, wherein the device is an organic light emitting device.

12. The organic electroluminescent device according to claim 2, wherein the device is a lighting panel.

13. The organic electroluminescent device according to claim 2, wherein the device is a backlight panel.

* * * * *